(12) United States Patent
Kim et al.

(10) Patent No.: US 12,226,224 B2
(45) Date of Patent: Feb. 18, 2025

(54) METHOD FOR DETECTING SLEEP APNEA AND ELECTRONIC DEVICE FOR SUPPORTING THE SAME

(71) Applicant: SAMSUNG ELECTRONICS CO., LTD., Suwon-si (KR)

(72) Inventors: Hyogil Kim, Suwon-si (KR); Jeongyup Han, Suwon-si (KR); Yumi Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 592 days.

(21) Appl. No.: 17/539,353

(22) Filed: Dec. 1, 2021

(65) Prior Publication Data
US 2022/0175311 A1 Jun. 9, 2022

Related U.S. Application Data

(63) Continuation of application No. PCT/KR2021/017380, filed on Nov. 24, 2021.

(30) Foreign Application Priority Data

Dec. 8, 2020 (KR) .......................... 10-2020-0170322

(51) Int. Cl.
*A61B 5/00* (2006.01)
*A61B 5/021* (2006.01)
*A61B 5/145* (2006.01)

(52) U.S. Cl.
CPC ............ *A61B 5/4818* (2013.01); *A61B 5/021* (2013.01); *A61B 5/14542* (2013.01); *A61B 5/681* (2013.01)

(58) Field of Classification Search
CPC ... A61B 5/4818; A61B 5/021; A61B 5/14542; A61B 5/681
See application file for complete search history.

(56) References Cited

U.S. PATENT DOCUMENTS 7,690,378 B1 4/2010 Turcott
2009/0234199 A1 9/2009 Takahashi et al.
(Continued)

FOREIGN PATENT DOCUMENTS

EP 1992280 A1 * 11/2008 ............... A61B 5/02
KR 10-2008-0099339 11/2008
(Continued)

OTHER PUBLICATIONS

International Search Report and Written Opinion dated Mar. 3, 2022 in corresponding International Application No. PCT/KR2021/017380.
(Continued)

*Primary Examiner* — Gary Jackson
*Assistant Examiner* — Sebastian X Lukjan
(74) *Attorney, Agent, or Firm* — Nixon & Vanderhye, P.C.

(57) ABSTRACT

According to various embodiments of the present disclosure, an electronic device may comprise: at least one sensor, and at least one processor functionally connected with the at least one sensor. The at least one processor may be configured to: detect, through the at least one sensor, that a user of the electronic device is in a sleep state; based on detecting that the user is in the sleep state, obtain first biometric information through the at least one sensor; identify whether a first value indicated by the obtained first biometric information is decreased so that a difference between the first value and a second value determined based on first biometric information obtained in a designated state is greater than or equal to a designated value; based on identifying that the first value is decreased so that the difference between the first value and the second value is greater than or equal to the designated value, obtain second biometric information through the at least one sensor; and provide information
(Continued)

related to sleep apnea based on the obtained second biometric information and second biometric information obtained in the designated state.

16 Claims, 12 Drawing Sheets

(56) References Cited

U.S. PATENT DOCUMENTS

| | | |
|---|---|---|
| 2011/0006901 A1 | 1/2011 | Cassidy |
| 2017/0209055 A1* | 7/2017 | Pantelopoulos ... A61B 5/02438 |
| 2018/0256096 A1* | 9/2018 | Galeev ................ A61B 5/0816 |
| 2022/0015716 A1 | 1/2022 | Lee et al. |

FOREIGN PATENT DOCUMENTS

| | | |
|---|---|---|
| KR | 10-1601895 | 3/2016 |
| KR | 101601895 B1 * | 3/2016 |
| KR | 10-2018-0056197 | 5/2018 |
| KR | 10-2018-0063577 | 6/2018 |
| KR | 10-2020-0113348 | 10/2020 |

OTHER PUBLICATIONS

Krainin, M.D., "Can Sleep Apnea Cause High Blood Pressure?", Singular Sleep—Rest Assured, Jan. 9, 2017, 10 pages.

* cited by examiner

METHOD FOR DETECTING SLEEP APNEA AND ELECTRONIC DEVICE FOR SUPPORTING THE SAME

CROSS-REFERENCE TO RELATED APPLICATIONS

This application is a continuation of International Application No. PCT/KR2021/017380, filed on Nov. 24, 2021, in the Korean Intellectual Property Receiving Office and claiming priority to Korean Patent Application No. 10-2020-0170322, filed on Dec. 8, 2020 in the Korean Intellectual Property Office, the disclosures of each of which is incorporated by reference herein in its entirety.

BACKGROUND

Field

The disclosure relates to a method for detecting sleep apnea and an electronic device supporting the same.

Description of Related Art

Portable electronic devices, such as smart phones, tablet personal computers (PCs), and wearable devices are recently in wide use, and the growth of technology is leading to advanced techniques for measuring biometric signals.

An electronic device may include various sensors capable of measuring the user's biosignals while being worn by the user and may provide various biometric information using the measured biosignals. For example, a wearable device may measure photoplethysmogram (PPG) signals using an optical method. The wearable device may provide biometric information about at least one of the pulse, oxygen saturation (also referred to as 'blood oxygen saturation') (saturation of peripheral oxygen (or peripheral oxygen saturation), SpO2), or blood pressure using the PPG signals.

Sleep apnea (e.g., obstructive sleep apnea (OSA)) may be a sleep disorder in which breathing is repeatedly stopped during sleep.

If apnea occurs in which breathing is stopped during sleep, the user's pulse may be bradycardia (e.g., a pulse with a pulse rate of about 30 to about 50 beats per minute) and, if breathing is resumed in the apnea state, the user's pulse may change from bradycardia to tachycardia (e.g., a pulse with a pulse rate of about 90 to about 120 beats). Further, as the user's pulse changes from bradycardia to tachycardia, oxygen saturation may change. The blood pressure measured during sleep apnea may also be different from the blood pressure measured in a stable state (e.g., in a state without sleep apnea).

Sleep apnea may be detected through a multi-parametric test using a specialized piece of equipment for detecting sleep apnea or, if a wearable device is used, sleep apnea may be detected by continuously measuring oxygen saturation while in a sleep state.

In the case of detecting sleep apnea through a multi-parametric test, there may be inconvenience in that the user has to use a specialized piece of equipment for detecting sleep apnea. Further, if the oxygen saturation is continuously measured while in the sleep state, a lot of power may be consumed in the wearable device, and it may be difficult to accurately measure the oxygen saturation due to the movement of the user wearing the wearable device.

SUMMARY

Embodiments of the disclosure provide a method for detecting sleep apnea by measuring at least one of oxygen saturation or blood pressure if the pulse (e.g., pulse rate) measured through a sensor while the user is in a sleep state meets a designated condition and an electronic device supporting the same.

According to various example embodiments of the disclosure, an electronic device may comprise: at least one sensor, and at least one processor functionally connected with the at least one sensor. The at least one processor may be configured to: detect, through the at least one sensor, that a user of the electronic device is in a sleep state; based on detecting that the user is in the sleep state, obtain first biometric information through the at least one sensor; identify whether a first value indicated by the obtained first biometric information is decreased so that a difference between the first value and a second value determined based on first biometric information obtained in a designated state is greater than or equal to a designated value; based on identifying that the first value is decreased so that the difference between the first value and the second value is greater than or equal to the designated value, obtain second biometric information through the at least one sensor; and provide information related to sleep apnea based on the obtained second biometric information and second biometric information obtained in the designated state.

According to various example embodiments of the disclosure, a method for detecting sleep apnea by an electronic device may comprise: detecting that a user of the electronic device is in a sleep state; based on detecting that the user is in the sleep state, obtaining first biometric information; identifying whether a first value indicated by the obtained first biometric information is decreased so that a difference between the first value and a second value determined based on first biometric information obtained in a designated state is greater than or equal to a designated value; based on identifying that the first value is decreased so that the difference between the first value and the second value is greater than or equal to the designated value, obtaining second biometric information; and providing information related to sleep apnea based on the obtained second biometric information and second biometric information obtained in the designated state.

According to various example embodiments of the disclosure, a method for performing functions using biosignals and an electronic device for supporting the same may provide information related to the user's sleep apnea by measuring at least one of the oxygen saturation or blood pressure when the pulse measured through a sensor while the user is in the sleep state meets a designated condition. Thus, the electronic device (e.g., a wearable device) may reduce power consumed to detect sleep apnea and may effectively provide the user with information related to sleep apnea.

BRIEF DESCRIPTION OF THE DRAWINGS

The above and other aspects, features and advantages of certain embodiments of the present disclosure will be more apparent from the following detailed description, taken in conjunction with the accompanying drawings, in which.

DETAILED DESCRIPTION

Figure 1:
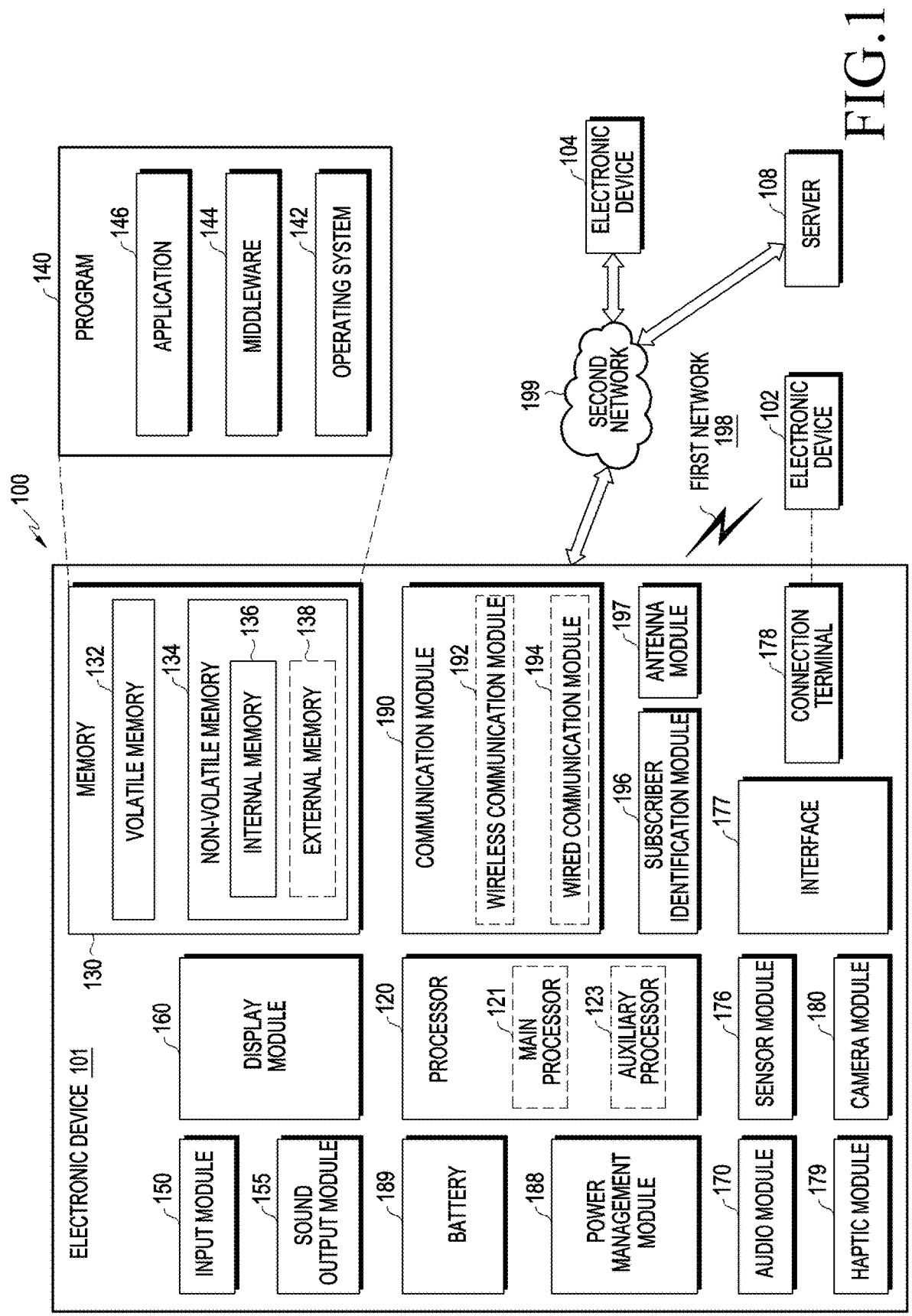
FIG. 1 is a block diagram illustrating an example electronic device in a network environment according to various embodiments.

FIG. 1 is a block diagram illustrating an example electronic device 101 in a network environment 100 according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In various embodiments, at least one (e.g., the connecting terminal 178) of the components may be omitted from the electronic device 101, or one or more other components may be added in the electronic device 101. According to an embodiment, some (e.g., the sensor module 176, the camera module 180, or the antenna module 197) of the components may be integrated into a single component (e.g., the display module 160).

The processor 120 may execute, for example, software (e.g., a program 140) to control at least one other component (e.g., a hardware or software component) of the electronic device 101 coupled with the processor 120, and may perform various data processing or computation.

According to an embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be configured to use lower power than the main processor 121 or to be specified for a designated function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. The artificial intelligence model may be generated via machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by other component (e.g., the processor 120) of the electronic device 101, from the outside (e.g., a user) of the electronic device 101. The input module 150 may include, for example, a microphone, a mouse, a keyboard, keys (e.g., buttons), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display 160 may include, for example, a display, a hologram device, or a projector and control circuitry to control a corresponding one of the display, hologram device, and projector. According to an embodiment, the display 160 may include a touch sensor configured to detect a touch, or a pressure sensor configured to measure the intensity of a force generated by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or motion) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device 104 via a first network 198 (e.g., a short-range communication network, such as Bluetooth™, wireless-fidelity (Wi-Fi) direct, or infrared data association (IrDA)) or a second network 199 (e.g., a long-range communication network, such as a legacy cellular network, a 5G network, a next-generation communication network, the Internet, or a computer network (e.g., local area network (LAN) or wide area network (WAN)). These various types of communication modules may be implemented as a single component (e.g., a single chip), or may be implemented as multi components (e.g., multi chips) separate from each other. The wireless communication module 192 may identify or authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device). According to an embodiment, the antenna module 197 may include one antenna including a radiator formed of a conductor or conductive pattern formed on a substrate (e.g., a printed circuit board (PCB)). According to an embodiment, the antenna module 197 may include a plurality of antennas (e.g., an antenna array). In this case, at least one antenna appropriate for a communication scheme used in a communication network, such as the first network 198 or the second network 199, may be selected from the plurality of antennas by, e.g., the communication module 190. The signal or the power may then be transmitted or received between the communication module 190 and the external electronic device via the selected at least one antenna. According to an embodiment, other parts (e.g., radio frequency integrated circuit (RFIC)) than the radiator may be further formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. The external electronic devices 102 or 104 each may be a device of the same or a different type from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra-low-latency services using, e.g., distributed computing or mobile edge computing. In an embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or health-care) based on 5G communication technology or IoT-related technology.

The electronic device according to various embodiments of the disclosure may be one of various types of electronic devices. The electronic devices may include, for example, a portable communication device (e.g., a smart phone), a computer device, a portable multimedia device, a portable medical device, a camera, a wearable device, a home appliance, or the like. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used herein, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. Some of the plurality of entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2A:
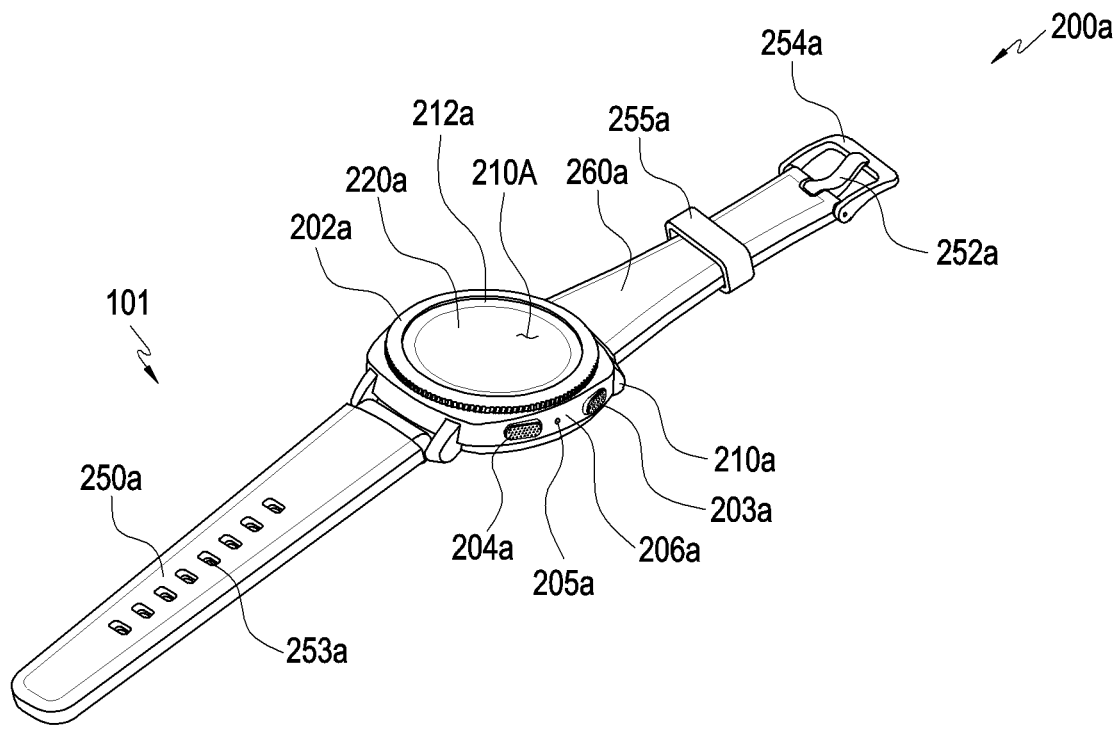
FIG. 2A is a front perspective view illustrating an electronic device according to various embodiments.
Figure 2B:
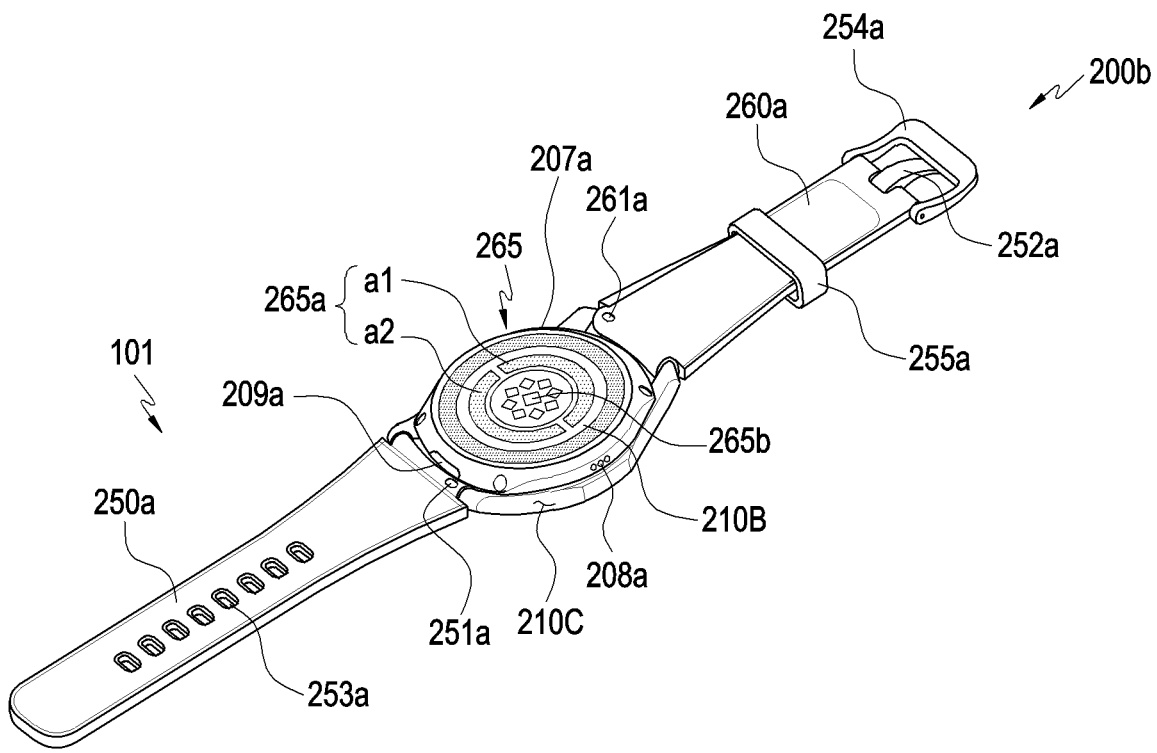
FIG. 2B is a rear perspective view illustrating the electronic device of FIG. 2A, according to various embodiments.

FIG. 2A is a front perspective view 200a illustrating an example electronic device 101 according to various embodiments, and FIG. 2B is a rear perspective view 100b illustrating the electronic device 101 of FIG. 2A according to various embodiments.

Referring to FIGS. 2A and 2B, an electronic device 101 according to an embodiment may include a housing 210a including a first surface (or a front surface) 210A, a second surface (or a rear surface) 210B, and a side surface 210C surrounding a space between the first surface 210A and the second surface 210B and wearing members (e.g., a strap or band) 250a and 260a connected to at least portions of the housing 210a and configured to be detachably worn on the user's body part (e.g., a wrist or ankle). According to an embodiment (not shown), the housing may denote a structure forming part of the first surface 210A, the second surface 210B, and the side surfaces 210C of FIGS. 2A and 2B. According to an embodiment, at least part of the first surface 210A may have a substantially transparent front plate 212a (e.g., a glass plate or polymer plate including various coat layers). The second surface 210B may be formed of a substantially opaque rear plate 207a. According to an embodiment, when the electronic device 101 includes a sensor module 265 disposed on the second surface 210B, the rear plate 207a may at least partially include a transparent area.

The rear plate 207a may be formed of, e.g., laminated or colored glass, ceramic, polymer, metal (e.g., aluminum, stainless steel (STS), or magnesium), or a combination of at least two thereof. The side surface 210C may be formed by a side bezel structure (or a "side member") 206a that couples to the front plate 212a and the rear plate 207a and includes a metal and/or polymer. According to an embodiment, the rear plate 207a and the side bezel structure 206a may be integrally formed together and include the same material (e.g., a metal, such as aluminum). The coupling members 250a and 260a may be formed of various materials in various shapes. A uni-body structure or multiple unit links which is flexible may be formed of fabric, leather, rubber, urethane, metal, ceramic, or a combination of at least two thereof.

According to an embodiment, the electronic device 101 may include at least one or more of a display 220a (refer to FIG. 2C), audio modules 205a and 208a, a sensor module 265, key input devices 202a, 203a, and 204a, and a connector hole 209a. According to an embodiment, the electronic device 101 may exclude at least one (e.g., the key input devices 202a, 203a, and 204a, connector hole 209a, or sensor module 265) of the components or may add other components.

According to an embodiment, the electronic device 101 may include a plurality of electrodes for measuring a biometric signal. At least one of the plurality of electrodes may be placed in at least one of the position of the key input device 202a, 203a, or 204a, the position of the bezel 206a, or the position of the display 220a or the housing 210a. Among the key input devices, the wheel key 202a may include a rotary bezel.

The display 220a may be viewable through a substantial portion of, e.g., the front plate 212a. The display 220a may have a shape corresponding to the shape of the front plate 212a, e.g., a circle, ellipse, or polygon. The display 220a may be coupled with, or disposed adjacent, a touch detection circuit, a pressure sensor capable of measuring the strength (pressure) of touches, and/or fingerprint sensor.

According to an embodiment, the display 220a may include at least one transparent electrode for measuring biometric signals among the plurality of electrodes for measuring biometric signals.

The audio modules 205a and 208a may include a microphone hole 205a and a speaker hole 208a. The microphone hole 205a may have a microphone inside to obtain external sounds. According to an embodiment, there may be a plurality of microphones to be able to detect the direction of a sound. The speaker hole 208a may be used for an external speaker or a receiver for phone talks. According to an embodiment, a speaker may be included without the speaker hole (e.g., a piezo speaker).

The sensor module 265 may produce an electrical signal or data value corresponding to the internal operation state or external environment state of the electronic device 101. The sensor module 265, e.g., a biometric sensor module 265 (e.g., an HRM sensor) placed on the second surface 210B of the housing 210a, may include an electrocardiogram (ECG) sensor 265a including at least two electrodes a1 and a2 for ECG measurement and a photoplethysmogram (PPG) sensor 265b for heartrate measurement. The electronic device 101 may include a sensor module not shown, e.g., at least one of a gesture sensor, a gyro sensor, a barometric sensor, a magnetic sensor, an acceleration sensor, a grip sensor, a color sensor, an infrared (IR) sensor, a biometric sensor, a temperature sensor, a humidity sensor, or an illuminance sensor.

The key input devices 202a, 203a, and 204a may include a wheel key 202a disposed on the first surface 210A of the housing 210*a* to be rotatable in at least one direction and/or side key buttons 203*a* and 204*a* disposed on the side surface 210C of the housing 210*a*. The wheel key 202*a* may have a shape corresponding to the shape of the front plate 212*a*. According to an embodiment, the electronic device 101 may exclude all or some of the above-mentioned key input devices 202*a*, 203*a*, and 204*a* and the excluded key input devices 202*a*, 203*a*, and 204*a* may be implemented in other forms, e.g., as soft keys on the display 220*a*. The connector hole 209*a* may receive a connector (e.g., a universal serial bus (USB) connector) for transmitting and receiving power and/or data to/from an external electronic device. Another connector hole (not shown) may be included for receiving a connector for transmitting and receiving audio signals to/from the external electronic device. The electronic device 101 may further include a connector cover (not shown) to cover at least part of, e.g., the connector hole 209*a* and preventing and/or reducing undesirable materials from entering the connector hole.

The coupling members 250*a* and 260*a* may detachably be fastened to at least portions of the housing 210*a* via locking members 251*a* and 261*a*. The locking members 251*a* and 261*a* may include components or parts for coupling, such as pogo pins, and, according to an embodiment, may be replaced with protrusions or recesses formed on/in the coupling members 250*a* and 260*a*. For example, the coupling members 250*a* and 260*a* may be coupled in such a manner as to be fitted into or over the recesses or protrusions formed on the housing 210. The coupling members 250*a* and 260*a* may include one or more of a fastening member 252*a*, fastening member coupling holes 253*a*, a band guide member 254*a*, and a band fastening ring 255*a*.

The fastening member 252*a* may be configured to allow the housing 110*a* and the coupling members 250*a* and 260*a* to be fastened to the user's body portion (e.g., wrist or ankle). The fastening member coupling holes 253*a* may fasten the housing 210*a* and the coupling members 250*a* and 260*a* to the user's body portion, corresponding to the fastening member 152*a*. The band guide member 254*a* may be configured to restrict movement of the fastening member 252*a* to a certain range when the fastening member 252*a* fits into one of the fastening member coupling holes 253*a*, thereby allowing the coupling members 250*a* and 260*a* to be tightly fastened onto the user's body portion. The band fastening ring 255*a* may limit the range of movement of the coupling members 250*a* and 260*a*, with the fastening member 252*a* fitted into one of the fastening member coupling holes 253*a*.

Figure 2C:
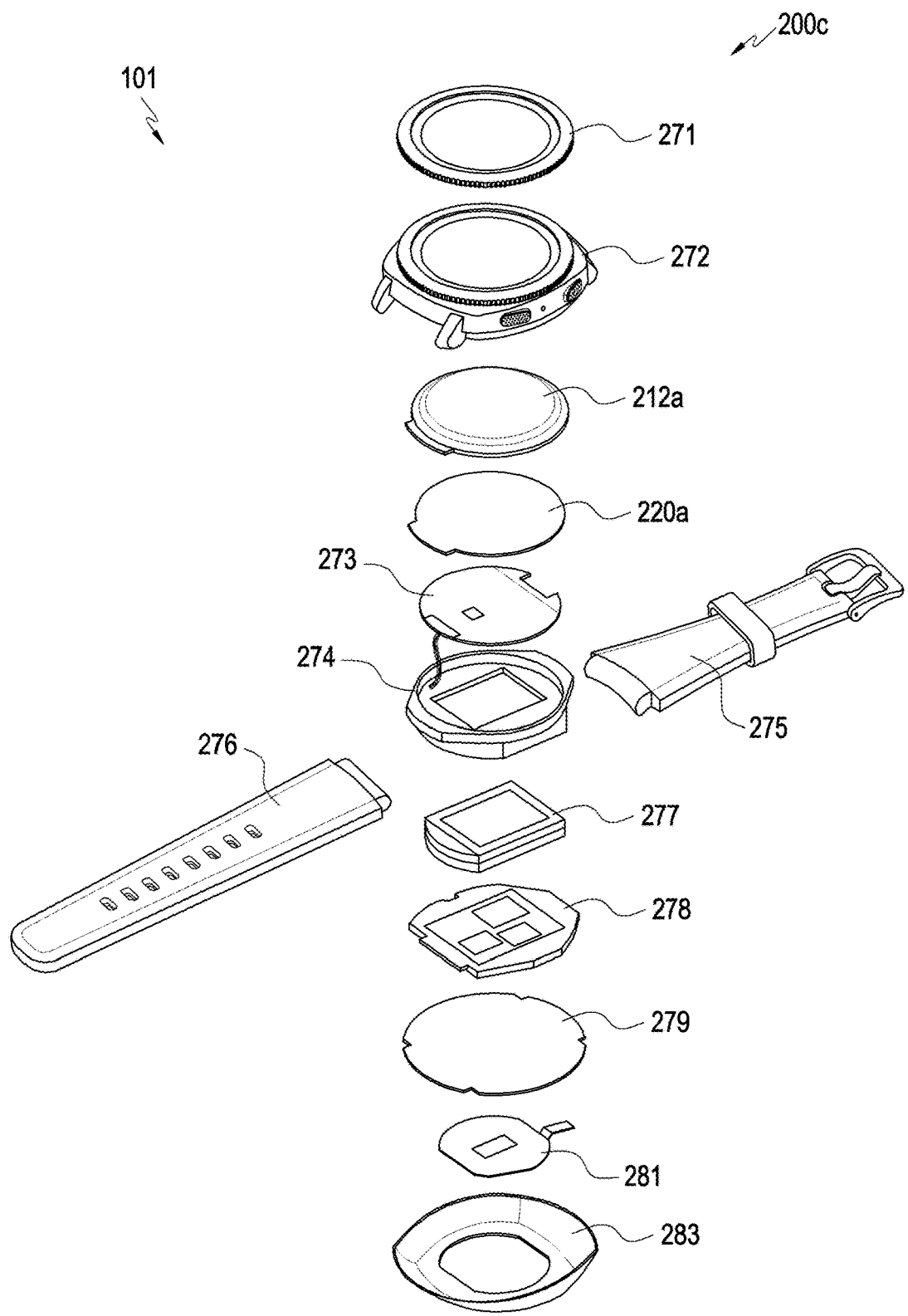
FIG. 2C is an exploded perspective view illustrating the electronic device of FIG. 2A, according to various embodiments.

FIG. 2C is an exploded perspective view 200*c* illustrating the electronic device 101 of FIG. 2A according to various embodiments.

Referring to FIG. 2C, the electronic device 101 may include a side bezel structure 272, a wheel key 271, a front plate 212*a*, a display 220*a*, a first antenna 273, a second circuit board 281, a supporting member 274 (e.g., a bracket), a battery 277, a printed circuit board 278, a sealing member 279, a rear plate 283, and wearing members 276 and 275. At least one of the components of the electronic device 101 may be the same or similar to at least one of the components of the electronic device 101 of FIG. 2A or 2B and duplicate description thereof may not be repeated here. The supporting member 274 may be disposed inside the electronic device 101 to be connected with the side bezel structure 272 or integrated with the side bezel structure 272. The supporting member 274 may be formed of, e.g., a metal and/or non-metallic material (e.g., polymer). The display 220*a* may be joined onto one surface of the supporting member 274, and the printed circuit board 278 may be joined onto the opposite surface of the supporting member 274. A processor, memory, and/or interface may be mounted on the printed circuit board 278. The processor may include one or more of, e.g., a central processing unit, an application processor, a graphic processing unit (GPU), a sensor processor, or a communication processor.

The memory may include, e.g., a volatile or non-volatile memory. The interface may include, e.g., a high definition multimedia interface (HDMI), a universal serial bus (USB) interface, a secure digital (SD) card interface, and/or an audio interface. The interface may electrically or physically connect, e.g., the electronic device 101 with an external electronic device and may include a USB connector, an SD card/multimedia card (MMC) connector, or an audio connector.

The battery 277 may be a device for supplying power to at least one component of the electronic device 101. The battery 277 may include, e.g., a primary cell which is not rechargeable, a secondary cell which is rechargeable, or a fuel cell. At least a portion of the battery 277 may be disposed on substantially the same plane as the printed circuit board 278. The battery 277 may be integrally or detachably disposed inside the electronic device 101.

The first antenna 273 may be disposed between the display 220*a* and the supporting member 274. The first antenna 273 may include, e.g., a near-field communication (NFC) antenna, a wireless charging antenna, and/or a magnetic secure transmission (MST) antenna. The first antenna 273 may perform short-range communication with an external device, wirelessly transmit/receive power necessary for charging, or transmit magnetic-based signals including payment data or short-range communication signals. According to an embodiment of the present disclosure, an antenna structure may be formed by a portion or combination of the side bezel structure 272 and/or the supporting member 274.

The second circuit board 281 may be disposed between the circuit board 278 and the rear plate 283. The second circuit board 281 may include, e.g., a near-field communication (NFC) antenna, a wireless charging antenna, and/or a magnetic secure transmission (MST) antenna. For example, the second circuit board 281 may perform short-range communication with an external device, wirelessly transmit/receive power necessary for charging, or transmit magnetic-based signals including payment data or short-range communication signals. According to an embodiment, an antenna structure may be formed of a portion or combination of the side bezel structure 272 and/or the rear plate 283. According to an embodiment, when the electronic device 101 includes a sensor module (e.g., the sensor module 265 of FIG. 2A), a sensor element (e.g., a photoelectric conversion element or electrode pad) separate from the second circuit board 281 or the sensor circuit disposed on the second circuit board 281 may be disposed. For example, an electronic component provided as the sensor module 165 may be disposed between the circuit board 278 and the rear plate 283.

The sealing member (e.g., seal) 279 may be positioned between the side bezel structure 272 and the rear plate 283. The sealing member 279 may be configured to block moisture or foreign bodies that may enter the space surrounded by the side bezel structure 272 and the rear plate 283, from the outside.

According to various embodiments described below, examples of measurable biometric signals may include electrical signals, such as electrocardiogram (ECG), electroencephalography (EEG), and electromyography (EMG), physical signals, such as blood pressure, body temperature, and PPG, and composition-related signals, such as blood glucose level, oxygen saturation, and body composition. However, the measurable biometric signals are not limited thereto. Further, although the description focuses primarily on an example of correcting external light for a PPG signal for optical heartbeat measurement, this is merely for convenience of description, and embodiments are not limited thereto.

Figure 3:
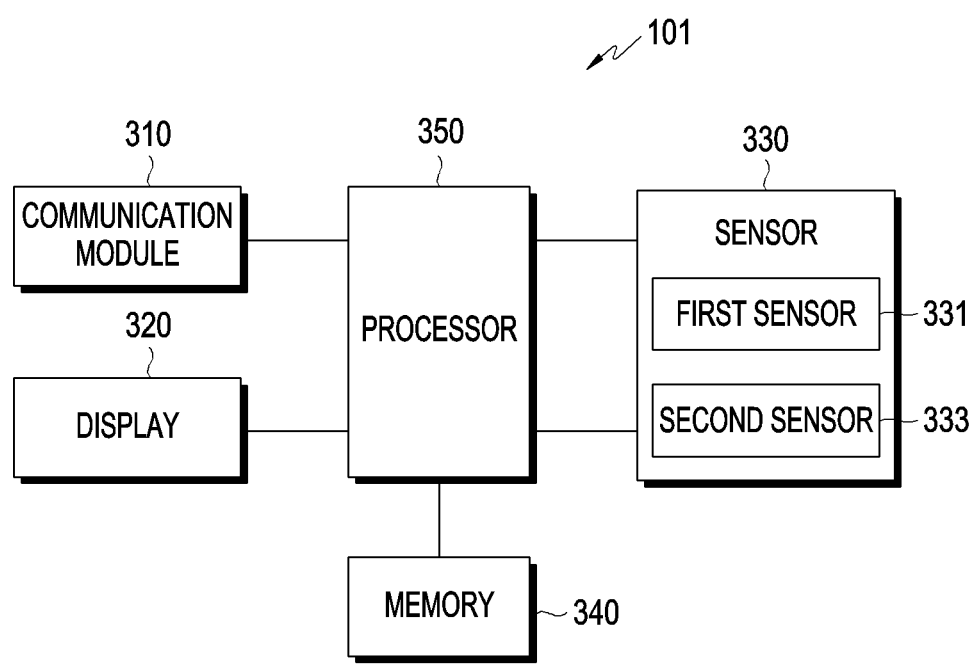
FIG. 3 is a block diagram illustrating an example configuration of an electronic device according to various embodiments.

FIG. 3 is a block diagram illustrating an example configuration of an electronic device 101 according to various embodiments.

Referring to FIG. 3, in an embodiment, an electronic device 101 may include a communication module (e.g., including communication circuitry) 310, a display 320, a sensor 330, a memory 340, and a processor (e.g., including processing circuitry) 350.

In an embodiment, the communication module 310 may be at least partially the same as or similar to the communication module 180 of FIG. 1. For example, the communication module 310 may transmit information related to various biometric information, obtained by the electronic device 101 in the user's sleep state (hereinafter, referred to as a 'sleep state'), to another electronic device (e.g., the electronic device 102, the electronic device 104, or the server 108). However, the information transmitted by the electronic device 101 to another electronic device through the communication module 310 is not limited to the above-described examples.

In an embodiment, the display 320 may be the same as or similar to the display module 160 of FIG. 1 or the display 220a of FIG. 2. In an embodiment, the display 320 may display information related to various biometric information obtained in the user's sleep state. For example, the display 320 may display at least one of information about the sleep time (e.g., from the time when the user started sleep (sleep onset time) to the time when the user ended sleep), information about the oxygen saturation obtained (e.g., measured) in the sleep state, information about the blood pressure obtained in the sleep state, or information related to sleep apnea occurring in the sleep state (e.g., information indicating that a phenomenon suspected of sleep apnea occurs in the sleep state). However, the information displayed through the display 320 is not limited to the above-described example.

In an embodiment, the sensor 330 may be the same as or similar to at least one of the sensor module 176 of FIG. 1 or the sensor module 265 of FIG. 2.

According to an embodiment, the sensor 330 may include a first sensor 331 and a second sensor 333.

In an embodiment, the first sensor 331 may detect the movement of the electronic device 101. For example, the first sensor 331 may detect the movement of the electronic device 101 (e.g., the magnitude of the movement of the electronic device 101 or a change in the movement of the electronic device 101) during a designated time, with the electronic device 101 worn on the user. In an embodiment, the first sensor 331 may include at least one of an acceleration sensor or a gyro sensor. However, the first sensor 331 is not limited to the above-described example, and any sensors 330 capable of detecting the movement of the electronic device 101 (or the user's movement) may be included. In an embodiment, the first sensor 331 may transfer information about the detected movement of the electronic device 101 to the processor 350.

In an embodiment, the second sensor 333 may be a biometric sensor for measuring biosignals from the user. In an embodiment, the second sensor 333 may be a photoplethysmogram (PPG) sensor.

In an embodiment, the PPG sensor may include a biosignal detector (not shown) and a biosignal processor (not shown).

In an embodiment, the biosignal detector for detecting PPG signals may include a light emitting unit and a light receiving unit. The light emitting unit may output light to the user's skin. The light emitting unit may output at least one of an infrared ray, red, green, and/or blue light sequentially or simultaneously. The light emitting unit may include at least one of a spectrometer, a vertical cavity surface emitting laser (VCSEL), a light emitting diode (LED), a white LED, and a white laser. The light receiving unit may receive the light (or an optical signal) input from the outside. For example, the light receiving unit may include at least a portion of the light (or an optical signal) reflected by the user's body tissue (e.g., skin, skin tissue, fat layer, vein, artery, and/or capillary) among the light output from the light emitting unit. Further, the light receiving unit may output a signal corresponding to the received light. For example, the light receiving unit 310 may include at least one of an avalanche photodiode (APD), a single photon avalanche diode (SPAD), a photodiode, a photomultiplier tube (PMT), a charge-coupled device (CCD), a complementary metal-oxide-semiconductor (CMOS) array, or a spectrometer. In an embodiment, the structure of at least one light receiving unit may be a reflective-type or a transmissive-type. However, the components included in the biosignal detector for detecting PPG signals are not limited to the light emitting unit and the light receiving unit.

In an embodiment, the biosignal processor may process the biosignal detected by the biosignal detector. In an embodiment, the biosignal processor (e.g., an analog front end) may include an amplifier for amplifying biosignals and an analog to digital converter (ADC) for converting analog biosignals into digital biosignals. However, the components included in the biosignal processor are not limited to the above-described amplifier and ADC. In an embodiment, although it is described that the biosignal processor is included in the sensor 330, embodiments are not limited thereto. The biosignal processor may be included in the processor 350.

In an embodiment, the second sensor 333 (e.g., a PPG sensor) may operate differently depending on the biometric information to be obtained. For example, if the biometric information to be obtained is the pulse in the sleep state, the PPG sensor may output infrared light through the light emitting unit and may operate at a sampling frequency of 25 Hz. As another example, if the biometric information to be obtained is the pulse in a non-sleep state (e.g., a stable state (the stable state is described below in detail)), the PPG sensor may output green light through the light emitting unit and may operate at a sampling frequency of 25 Hz. As another example, if the biometric information to be obtained is oxygen saturation, the PPG sensor may output red light (or red light and infrared light) through the light emitting unit and may operate at a sampling frequency of 100 Hz. As another example, if the biometric information to be obtained is blood pressure, the PPG sensor may output green light through the light emitting unit and may operate at a sampling frequency of 100 Hz. However, examples in which the PPG sensor operates differently depending on the biometric information to be obtained are not limited to the above-described examples. In an embodiment, the PPG sensor may operate to obtain a plurality of biometric information, e.g., at least two or more pieces of biometric information among, e.g., pulse, oxygen saturation, and blood pressure. For example, the PPG sensor may operate to simultaneously obtain pulse rate, oxygen saturation, and blood pressure.

In the above-described examples, although it is illustrated by way of non-limiting example that one PPG sensor obtains at least two or more pieces of biometric information among a plurality of biometric information (e.g., pulse, oxygen saturation, and blood pressure), embodiments are not limited thereto.

In an embodiment, the second sensor 333 may include a laser diode (LD) and an image sensor.

In an embodiment, the second sensor 333 may include a plurality of sensors 330 for obtaining each of a plurality of biometric information. For example, the second sensor 333 may include independent (or separate) sensors for obtaining each of a plurality of biometric information, such as a sensor for obtaining the pulse, a sensor for obtaining oxygen saturation, and a sensor for obtaining blood pressure.

In FIG. 3, the second sensor 333 is included in the electronic device 101 as an example, but embodiments are not limited thereto. In an embodiment, at least some of the plurality of biometric information may be obtained through another electronic device (e.g., a ring-shaped wearable electronic device that may be worn on the user). For example, a sensor for obtaining the pulse may be included in the electronic device 101, a sensor 330 for obtaining the oxygen saturation may be included in a first wearable device, and a sensor for obtaining the blood pressure may be included in a second wearable device different from the first wearable device. In this case, the electronic device 101, the first wearable device, and the second wearable device may simultaneously obtain biometric information. The biometric information obtained by each of the first wearable device and the second wearable device may be transmitted to the electronic device 101 (or the server 108).

According to an embodiment, the memory 340 may be included in the memory 130 of FIG. 1.

In an embodiment, the memory 340 may store the obtained biometric information. The biometric information stored in the memory 340 is described in greater detail below.

According to an embodiment, the processor 350 may be included in the processor 120 of FIG. 1. In an embodiment, the processor 350 may include one or more processors.

In an embodiment, the processor 350 may include various processing circuitry and control the overall operation of performing the method for detecting sleep apnea.

Hereinafter, operations performed by the processor 350 are described in greater detail below with reference to FIGS. 4, 5, 6, 7, 8, 9, 10, 11, and 12.

According to various example embodiments of the disclosure, an electronic device may comprise at least one sensor, and at least one processor functionally connected with the at least one sensor. The at least one processor may be configured to detect, through the at least one sensor, that a user of the electronic device is in a sleep state; based on detecting that the user is in the sleep state, obtain first biometric information through the at least one sensor, identify whether a first value indicated by the obtained first biometric information is decreased so that a difference between the first value and a second value determined based on first biometric information obtained in a designated state is a designated value or more, based on the first value being decreased so that the difference between the first value and the second value is the designated value or more, obtain second biometric information through the at least one sensor, and provide information related to sleep apnea based on the obtained second biometric information and second biometric information obtained in the designated state.

According to various example embodiments, the first biometric information may include a pulse, and the second biometric information may include at least one of an oxygen saturation or a blood pressure.

According to various example embodiments, the at least one processor may be configured to determine the second value of the first biometric information based on the first biometric information obtained in the stable state during non-sleep as the designated state.

According to various example embodiments, the at least one processor may be configured to obtain a plurality of first biometric information over a plurality of times in the stable state during non-sleep, through the at least one sensor and determine a smallest value among a plurality of values indicated by each of the plurality of first biometric information, as a second value of the first biometric information.

According to various example embodiments, the at least one processor may be configured to obtain a plurality of first biometric information, through the at least one sensor, while the user is in the sleep state as the designated state and determine an average of values, except for values not less than a designated first value and not more than a designated second value, among values indicated by the plurality of first biometric information, as a second value of the first biometric information.

According to various example embodiments, the at least one processor may be configured to identify a time when the first value is reduced so that the difference between the first value and the second value is the designated value or more and obtain the second biometric information, through the at least one sensor, during a designated time from the time.

According to various example embodiments, the at least one processor may be configured to identify a third value indicated by the obtained second biometric information, identify a fourth value of the second biometric information determined based on the second biometric information obtained in the stable state during non-sleep as the designated state, and provide information related to the sleep apnea, based on the third value and the fourth value.

According to various example embodiments, the at least one processor may be configured to identify whether a pattern indicated by the first biometric information corresponds to a designated pattern, identify whether the pattern corresponding to the designated pattern is detected a designated number of times during a designated time, and based on the pattern corresponding to the designated pattern being detected the designated number of times during the designated time, identify whether the first value is reduced so that the difference between the first value and the second value is the designated value or more.

According to various example embodiments, the at least one processor may be configured to identify whether a pattern indicated by the first biometric information corresponds to a designated pattern, identify a cycle of the pattern based on the pattern corresponding to the designated pattern, and obtain the second biometric information, through the at least one sensor, based on the cycle of the pattern.

According to various example embodiments, the at least one processor may be configured to control the at least one sensor to operate at a first sampling frequency to obtain the first biometric information and control the at least one sensor to operate at a second sampling frequency higher than the first sampling frequency to obtain the second biometric information.

Figure 4:
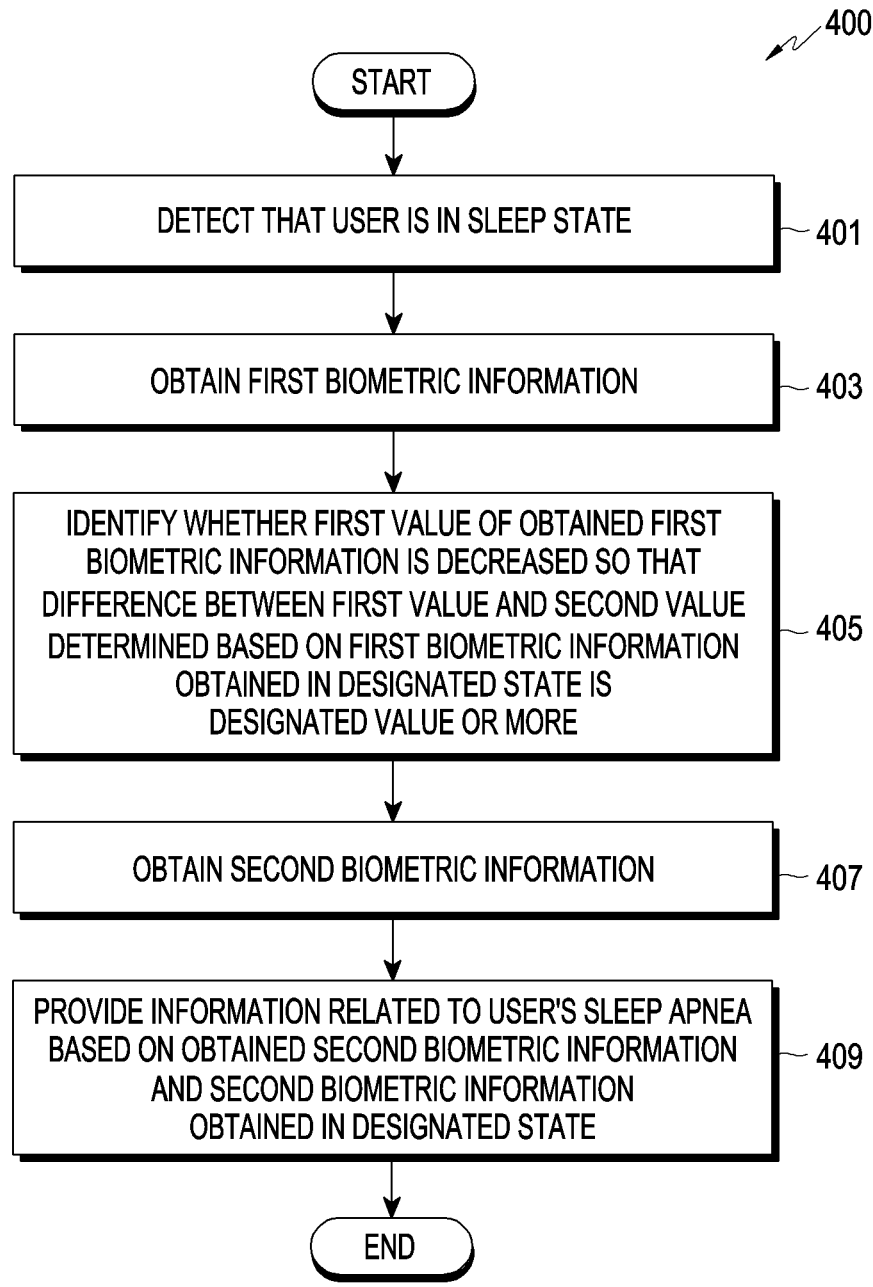
FIG. 4 is a flowchart illustrating an example method for detecting sleep apnea, according to various embodiments.

FIG. 4 is a flowchart 400 illustrating an example method for detecting sleep apnea, according to various embodiments.

Referring to FIG. 4, in operation 401, in an embodiment, the processor 350 may detect, through the sensor 330, that the user of the electronic device 101 is in a sleep state.

In an embodiment, the processor 350 may obtain, through the first sensor 331 (e.g., an acceleration sensor), information about the movement of the electronic device 101 (e.g., the magnitude of the movement of the electronic device 101 or a change in the movement of the electronic device 101). The processor 350 may identify whether the magnitude of the movement of the electronic device 101 is equal to or less than a threshold magnitude for a designated time, based on the information about the movement of the electronic device 101. If it is identified that the magnitude of the movement of the electronic device 101 is equal to or less than the threshold magnitude for the designated time, the processor 350 may determine that the user has started sleep. However, the method by which the processor 350 detects that the user is in the sleep state is not limited to the above-described example.

In operation 403, in an embodiment, if it is detected that the user is in the sleep state, the processor 350 may obtain the user's first biometric information through the sensor 330.

In an embodiment, the processor 350 may obtain a biosignal (e.g., a PPG signal) through the second sensor 333 (e.g., a PPG sensor). The processor 350 may obtain biometric information (e.g., a pulse) (hereinafter, referred to as 'first biometric information') based on the biosignal.

In an embodiment, the processor 350 may obtain the first biometric information while the user is in the sleep state. For example, the processor 350 may obtain the pulse from the time when the user starts sleep to the time when the user ends the sleep (e.g., until it is detected that the sleep state ends).

In an embodiment, the processor 350 may control the second sensor 333 to obtain the first biometric information. For example, the processor 350 may control the PPG sensor so that the light emitting unit of the PPG sensor outputs infrared light and operates at a sampling frequency of 25 Hz so as to obtain a pulse (e.g., pulse rate) in the sleep state. However, the light of the light emitting unit of the PPG sensor used to obtain the pulse in the sleep state is not limited to infrared light, and the light of the light emitting unit of the PPG sensor used to obtain the pulse in the sleep state may be green light.

In an embodiment, the processor 350 may identify a change in the first biometric information while the first biometric information is obtained. For example, the processor 350 may identify a change in the first biometric information based on data related to the biometric information obtained during the designated time using a sliding window scheme. Examples of the operation of identifying the change in the first biometric information using the sliding window scheme are described below in detail with reference to FIG. 6.

In operation 405, in an embodiment, the processor 350 may identify whether a first value indicated by the obtained first biometric information (hereinafter, referred to as a 'first value') decreases (or is decreasing) so that the difference between the first value and a second value determined based on the first biometric information obtained in a designated state (hereinafter, referred to as a 'second value') is a designated value or more.

In an embodiment, the processor 350 may determine the second value to be compared with the first value based on the first biometric information obtained in a stable state during non-sleep as the designated state.

In an embodiment, the stable state (also referred to as a resting state) may be a state in which the user's movement (e.g., a movement of the electronic device 101 when the electronic device 101 is worn by the user) is not detected. In an embodiment, the stable state may be a state in which the magnitude of the user's movement is less than or equal to a threshold magnitude (e.g., a state in which the magnitude of the movement of the electronic device 101 lasts as being equal to or less than the threshold magnitude during the designated time when the electronic device 101 is worn on the user). For example, the stable state may be a state in which the user's movement is not detected immediately after the sleep state is terminated.

In an embodiment, the processor 350 may detect, through the first sensor 331, that the user is in the non-sleep state (e.g., in a state in which the user is not in the sleep state) and the stable state. When it is detected that the user is in the non-sleep state and the stable state (hereinafter, interchangeably used with 'stable state during non-sleep'), the processor 350 may obtain the first biometric information (e.g., the pulse) through the second sensor 333 (e.g., the PPG sensor) during a designated time (or while in the non-sleep state and the stable state). In an embodiment, the processor 350 may obtain the first biometric information through the second sensor 333 whenever it is detected that the user is in the non-sleep state and the stable state. For example, if it is detected multiple times that the user is in the stable state during non-sleep, the processor 350 may obtain the first biometric information through the second sensor 333 in each of the plurality of stable states.

In an embodiment, if a plurality of first biometric information is obtained over a plurality of times in the stable state during non-sleep, the processor 350 may determine the second value of the first biometric information based on the plurality of first biometric information.

In an embodiment, if the plurality of first biometric information is obtained over a plurality of times in the stable state during non-sleep, the processor 350 may determine that the smallest (or lowest) value of the values indicated by each of the plurality of first biometric information is the second value of the first biometric information. For example, if a first pulse rate (e.g., 100 beats per minute (BPM)) is obtained in a first stable state during non-sleep, a second pulse rate (e.g., 90 BPM) is obtained in a second stable state during non-sleep, and a third pulse rate (e.g., 110 BPM) is obtained in a third stable state during non-sleep, the processor 350 may determine that the lowest one, i.e., the second pulse rate, among the first to third pulse rates is the second value of the first biometric information.

In an embodiment, if a plurality of first biometric information is obtained over a plurality of times in the stable state during non-sleep, the processor 350 may determine that the largest (or highest) value among the values indicated by each of the plurality of first biometric information is the second value of the first biometric information.

In an embodiment, if a plurality of first biometric information is obtained over a plurality of times in the stable state during non-sleep, the processor 350 may determine that the average of the values indicated by each of the plurality of first biometric information is the second value of the first biometric information. For example, if a first pulse rate (e.g., 100 beats per minute (BPM)) is obtained in a first stable state during non-sleep, a second pulse rate (e.g., 90 BPM) is obtained in a second stable state during non-sleep, and a third pulse rate (e.g., 110 BPM) is obtained in a third stable state during non-sleep, the processor 350 may determine that the average, e.g., 100 BPM, of the first to third pulse rates is the second value of the first biometric information.

In an embodiment, the processor 350 may obtain a plurality of first biometric information over a plurality of times in the stable state during non-sleep, daily (e.g., on a daily cycle) during a designated period (e.g., about one week). The processor 350 may determine (e.g., calculate) the average of the plurality of first biometric information over a plurality of times in the stable state during non-sleep, daily, during the designated period (e.g., the average of the values indicated by the plurality of first biometric information obtained in each stable state during non-sleep during each day in the designated period) (hereinafter, also referred to as a 'daily resting average value'). The processor 350 may determine the lowest value among the average values of the plurality of first biometric information about each of the days included in the designated period as the second value of the first biometric information. For example, the processor 350 may obtain a plurality of pulse rates over a plurality of times in the stable state during non-sleep, every day for one week and may determine the average value (daily resting average value) of the plurality of obtained pulse rates. The processor 350 may determine the lowest value of the average values of seven pulse rates (daily resting average values calculated for seven days) determined on each of the seven days of the week, as the second value of the first biometric information. However, embodiments are not limited thereto. The processor 350 may determine that the highest value of the average values of the plurality of first biometric information about each of the days included in the designated period or the average of the average values of the plurality of first biometric information about each of the days included in the designated period is the second value of the first biometric information.

In an embodiment, the processor 350 may store the second value determined based on the first biometric information obtained in the stable state during non-sleep, as the designated state, in the memory 340 or may transmit the second value through the communication module 310 to another electronic device (e.g., the electronic device 102, the electronic device 104, or the server 108).

In an embodiment, the processor 350 may update the second value as the first biometric information is obtained in the stable state during non-sleep. For example, the processor 350 may determine the second value based on a plurality of first biometric information obtained over a plurality of times in the stable state during non-sleep from the day (e.g., yesterday) before the current day (today) to a time before the designated period and, if the first biometric information is obtained in the stable state during non-sleep for the current day, redetermine (e.g., update) the second value based on a plurality of first biometric information obtained over a plurality of times in the stable state during non-sleep from the current day to the period before the designated period.

In an embodiment, the processor 350 may determine the second value based on the first biometric information obtained in the stable state during non-sleep and may reflect a weight to the second value to redetermine (e.g., update) the second value based on the first biometric information corresponding to the sleep state.

Hereinafter, a scheme for determining the second value to be compared with the first value based on the first biometric information obtained in the stable state during non-sleep as the designated state is referred to as a 'first scheme'.

In an embodiment, the processor 350 may determine the second value to be compared with the first value (e.g., the value indicated by the currently obtained first biometric information), based on the first biometric information obtained during the sleep state, as the designated state, (e.g., obtained and stored in the memory 340).

In an embodiment, the processor 350 may obtain a plurality of first biometric information through the second sensor 333 while the user is in the sleep state. The processor 350 may determine the second value based on the values indicated by the first biometric information in a designated range from among the values indicated by the plurality of first biometric information obtained while in the sleep state. For example, the processor 350 may determine, as the second value, the average of the remaining values except for the values not less than a designated value (e.g., not less than the minimum pulse rate (about 90 beats) of tachycardia (e.g., a pulse with a pulse rate of about 90 beats to about 120 beats)) and the values not more than the designated value (e.g., not more than the maximum pulse rate (about 50 beats) of bradycardia (e.g., a pulse with a pulse rate of about 30 beats to about 50 beats per minute)) among the values indicated by the first biometric information obtained while in the sleep state.

In an embodiment, the processor 350 may obtain the plurality of first biometric information obtained while the user is in the sleep state daily (every day) during a designated period (e.g., about one week). The processor 350 may determine the average value of the values indicated by the first biometric information in a designated range among the values indicated by the plurality of first biometric information obtained while in the sleep state, daily during the designated period (e.g., the average value in a range less than a designated value and more than a designated value among the values indicated by the plurality of first biometric information obtained in the sleep state, daily, during the designated period) (hereinafter, referred to as a 'daily sleep average value'). The processor 350 may determine the average value of the plurality of average values determined during a designated period (e.g., the average of the daily sleep average values determined every day for one week) as the second value.

Hereinafter, a scheme for determining the second value to be compared with the first value based on the first biometric information obtained in the sleep state as the designated state is referred to as a 'second scheme'.

In an embodiment, the processor 350 may determine the second value to be compared with the first value using the first scheme or the second scheme.

In an embodiment, the processor 350 may perform an operation for detecting sleep apnea based on the second value determined using the first scheme, and then, if the designated condition is met, the processor 350 may perform an operation for detecting sleep apnea based on the second value determined using the second scheme. For example, the processor 350 may perform an operation for detecting sleep apnea based on the second value determined using the first scheme during a predetermined period (e.g., during a predetermined period after the user purchases the electronic device 101 or during a predetermined period after first starting the operation of obtaining first biometric information). The processor 350 may obtain a plurality of first biometric information in the sleep state to determine the second value by the second scheme during the predetermined period. If the amount of the plurality of first biometric information obtained using the second scheme (e.g., in the sleep state) is not less than a designated amount, the processor 350 may determine the second value using the second scheme and perform an operation for detecting sleep apnea using the determined second value, instead of performing an operation for detecting sleep apnea based on the second value determined using the first scheme.

In an embodiment, the processor 350 may identify whether the first value indicated by the first biometric information obtained (or being currently obtained) is decreased so that the difference between the first value and the second value is decreased by a designated value or more.

The operation in which the processor 350 identifies whether the first value is decreased so that the difference between the first value and the second value is decreased by the designated value or more is described in greater detail below with reference to FIGS. 5 and 6.

Figure 5:
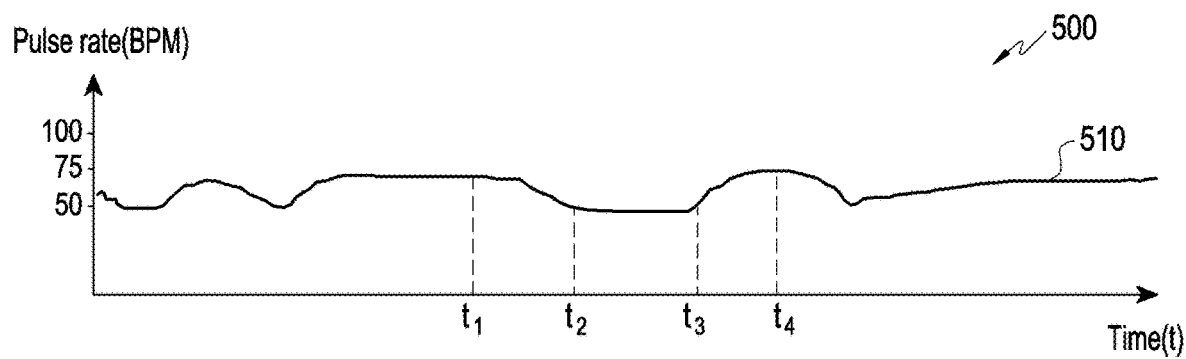
FIG. 5 is a graph illustrating a change in pulse rate when apnea occurs in a sleep state, according to various embodiments.

FIG. 5 is a graph 500 illustrating a change in pulse rate when apnea occurs in a sleep state, according to various embodiments.

Figure 6:
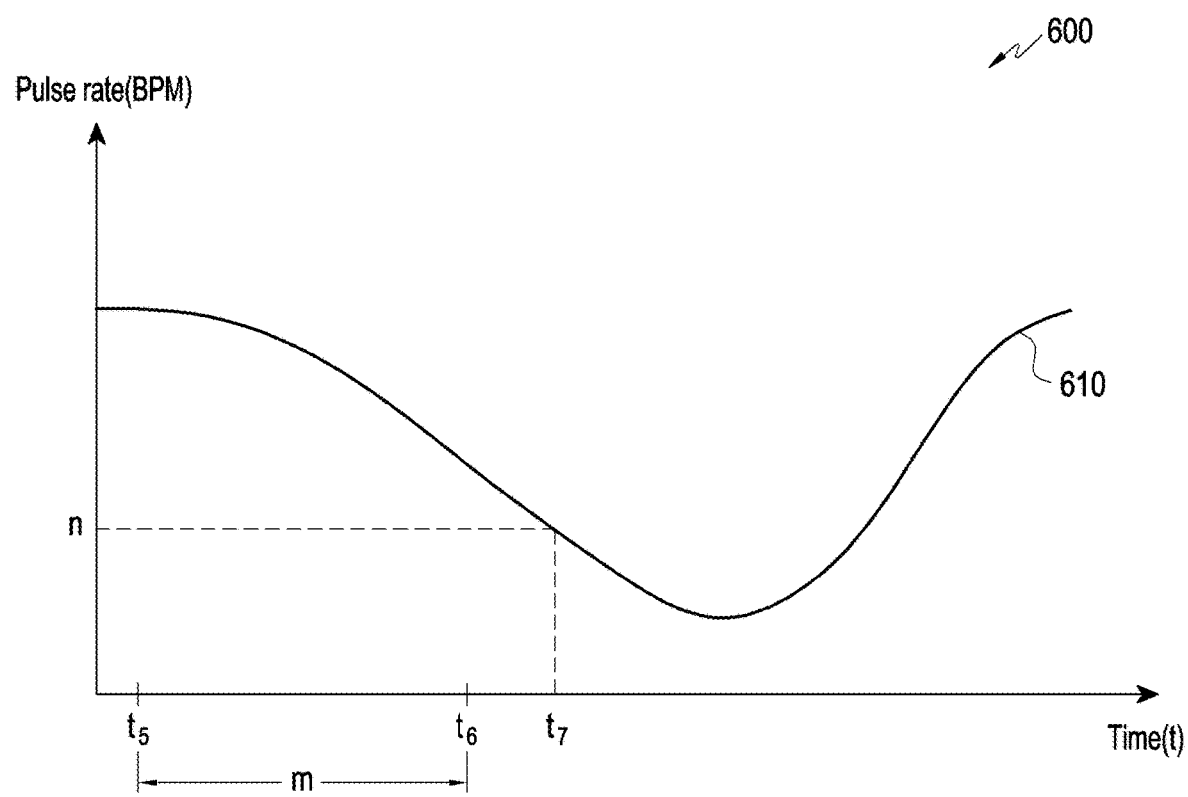
FIG. 6 is a graph illustrating an example method for detecting apnea in a sleep state, according to various embodiments.

FIG. 6 is a graph 600 illustrating an example method for detecting apnea in a sleep state, according to various embodiments.

Referring to FIGS. 5 and 6, according to an embodiment, a pattern as shown by the line 510 of FIG. 5, which indicates the pulse rate obtained in the sleep state may occur in which the user's pulse is bradycardia (e.g., a pulse with a pulse rate of about 30 to about 50 beats per minute) and, if breathing is resumed in the apnea state, the user's pulse changes from bradycardia to tachycardia (e.g., a pulse with a pulse rate of about 90 to about 120 beats). For example, in FIG. 5, if apnea occurs during sleep, the user's pulse rate may be reduced, such as a change in pulse rate from a first time t1 to a second time t2 and, if breathing is resumed, the user's pulse rate may be increased, such as a change in pulse rate from a third time t3 to a fourth time t4.

In an embodiment, the processor 350 may identify a time (e.g., the second time t2) when the first value (e.g., the pulse rate being obtained) indicated by the first biometric information is in a reduced state (or the pulse rate being obtained is in a reducing state), and the difference between the first value and the second value (e.g., the pulse rate obtained in the designated state and stored in the memory 340) is a designated value (e.g., about 20 BPM).

In an embodiment, the processor 350 may identify whether the first value indicated by the first biometric information is reduced using the sliding window scheme. For example, in FIG. 6, the line 610 may represent the pulse rate obtained over time in the sleep state. The processor 350 may summate the values (e.g., pulse rates) indicated by the plurality of first biometric information obtained during a designated time period (e.g., a time m) from the current time (e.g., a sixth time t6) to a time (e.g., a fifth time t5) before the current time (the sixth time t6) during sleep. If the summated value from the current time (e.g., the sixth time t6) is smaller than the sum of the values (e.g., pulse rates) indicated by the plurality of first biometric information obtained during a designated time period (e.g., time m), at a time before the current time (e.g., the sixth time t6) (e.g., a preset time (e.g., 1 second) before the sixth time t6), the processor 350 may identify whether the first value (e.g., the pulse rate at the current time) indicated by the first biometric information at the current time (e.g., the sixth time t6) is reduced as compared with the value indicated by the first biometric information at the time before the current time. In an embodiment, the designated time period (e.g., the time m) may be referred to as a sliding window. In an embodiment, the processor 250 may move the sliding window over time and identify whether the first value indicated by the first biometric information has been reduced (or is being reduced) based on a change in the values of the first biometric information included in the sliding window (e.g., obtained during the sliding window) (e.g., the values of the first biometric information included in the sliding window (e.g., about 1 second) at the current time). In an embodiment, in FIG. 6, the processor 350 may identify that the difference between the first value (e.g., n) indicated by the first biometric information obtained at the current time (e.g., a time t7) during sleep and the second value obtained in the designated state is the same as a designated value (e.g., about 20 BPM) (or not less than the designated value) and the first value indicated by the first biometric information has been reduced.

Referring back to FIG. 4, in operation 407, according to an embodiment, if the first value indicated by the first biometric information is reduced so that the difference between the first value and the second value becomes a designated value or more, the processor 350 may obtain second biometric information through the sensor 330. For example, if the first value is reduced so that the difference between the first value and the second value becomes the designated value or more, the processor 350 may obtain the second biometric information (e.g., at least one of oxygen saturation or blood pressure) through the second sensor 333 (e.g., a PPG sensor).

According to an embodiment, at the time when the first value is reduced so that the difference between the first value and the second value becomes the designated value or more, the processor 350 may start the operation of obtaining the second biometric information (e.g., at least one of oxygen saturation or blood pressure) through the second sensor 333 (e.g., a PPG sensor). For example, at the time when the first value is reduced so that the difference between the first value and the second value becomes the designated value or more, the processor 350 may control the PPG sensor to output red light (or red light and infrared light) through the light emitting unit and to operate at a sampling frequency of 100 Hz to obtain the oxygen saturation (e.g., to sample the PPG signal at a sampling frequency of 100 Hz to obtain the oxygen saturation). As another example, at the time when the first value is reduced so that the difference between the first value and the second value becomes the designated value or more, the processor 350 may control the PPG sensor to output green light through the light emitting unit and to operate at a sampling frequency of 100 Hz to obtain the blood pressure (e.g., to sample the PPG signal at a sampling frequency of 100 Hz to obtain the blood pressure). As another example, at the time when the first value is reduced so that the difference between the first value and the second value becomes the designated value or more, the processor 350 may control the PPG sensor to output red light through the light emitting unit and to operate at a sampling frequency of 100 Hz to obtain the oxygen saturation while simultaneously outputting green light through the light emitting unit and operating at a sampling frequency of 100 Hz to obtain the blood pressure.

According to an embodiment, every time the first value is reduced so that the difference between the first value and the second value becomes the designated value or more, the processor 350 may obtain second biometric information through the sensor 333 during a designated time. For example, every time the first value is reduced so that the difference between the first value and the second value becomes the designated value or more, the processor 350 may obtain at least one of the oxygen saturation or the blood pressure during a designated time (e.g., 10 seconds or more) from the time of the reduction. In an embodiment, the processor 350 may determine (e.g., set) the designated time (e.g., about 10 seconds or more) for obtaining the second biometric information based on a time specified by a professional institution (e.g., a medical professional institution) as the time when sleep apnea (e.g., obstructive sleep apnea) occurs. In an embodiment, the processor 350 may determine the designated time for obtaining the second biometric information based on a time when a change in the second biometric information necessary for detecting an occurrence of sleep apnea may be obtained.

According to an embodiment, the processor 350 may perform the operation of obtaining the second biometric information (e.g., at least one of the oxygen saturation or the blood pressure) through the second sensor 333 (e.g., a PPG sensor) until the user's sleep state terminates. For example, if the operation of obtaining the second biometric information (e.g., at least one of the oxygen saturation or the blood pressure) through the second sensor 333 (e.g., a PPG sensor) begins, the processor 350 may obtain the second biometric information during the designated time through the second sensor 333 every time the first value is reduced so that the difference between the first value and the second value becomes the designated value or more, until the termination of the user's sleep state is detected.

Figure 7:
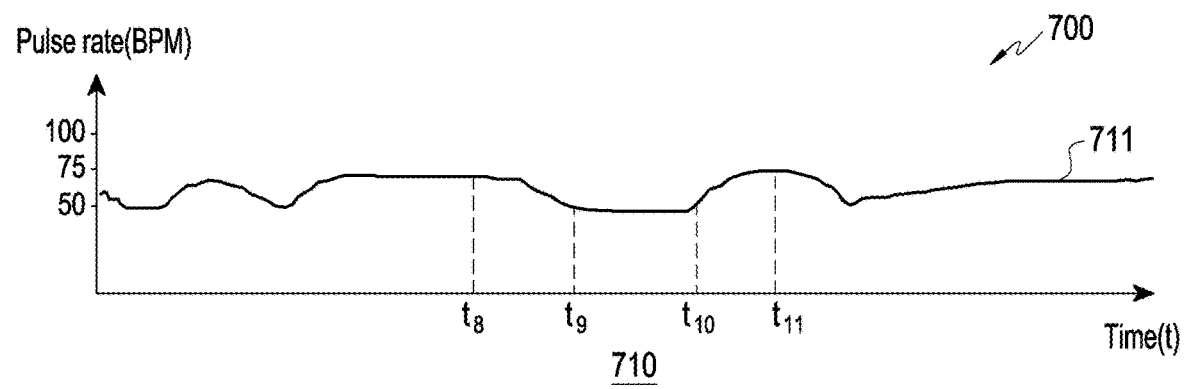
FIG. 7 includes graphs illustrating a relationship between pulse rate and oxygen saturation when apnea occurs in a sleep state, according to various embodiments.
Figure 7:
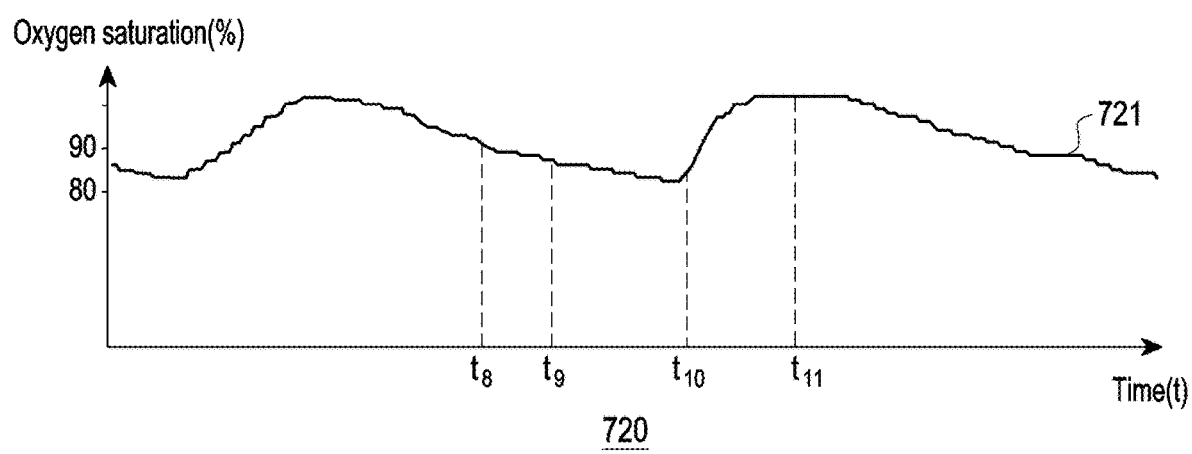

FIG. 7 includes graphs 700 illustrating a relationship between pulse rate and oxygen saturation when apnea occurs in a sleep state, according to various embodiments.

Referring to FIG. 7, in an embodiment, reference number 710 may indicate the pulse 711 obtained in the sleep state, and reference number 720 may indicate the oxygen saturation 721 obtained in the sleep state. In an embodiment, as illustrated in FIG. 7, if apnea occurs during sleep, the value of oxygen saturation may decrease as the pulse rate reduces from an eighth time t8 to a ninth time t9. If breathing is resumed from apnea, the pulse rate increases from a tenth time t10 to an eleventh time t11 so that the value of oxygen saturation may increase. In an embodiment, as illustrated in FIG. 7, if apnea occurs during sleep, a change in oxygen saturation (or the pattern of oxygen saturation) may correspond to a change in pulse (or the pattern of pulse). Although not clearly shown in FIG. 7, in an embodiment, a predetermined time after a change in pulse (e.g., pulse rate) occurs (e.g., after delayed for the predetermined time), a change in oxygen saturation (e.g., the numerical value of saturation) may occur.

In an embodiment, when apnea occurs during sleep, a change in oxygen saturation corresponds to a change in pulse rate. Thus, the processor 350 may reduce the power consumption in the electronic device 101 by obtaining the oxygen saturation through the sensor 330 during a designated time and detecting sleep apnea based on the oxygen saturation obtained during the designated time if the first value indicated by the first biometric information is reduced so that the difference between the first value and the second value becomes a designated value or more, without the need for obtaining the oxygen saturation over the entire time during which the user is in the sleep state.

Figure 8:
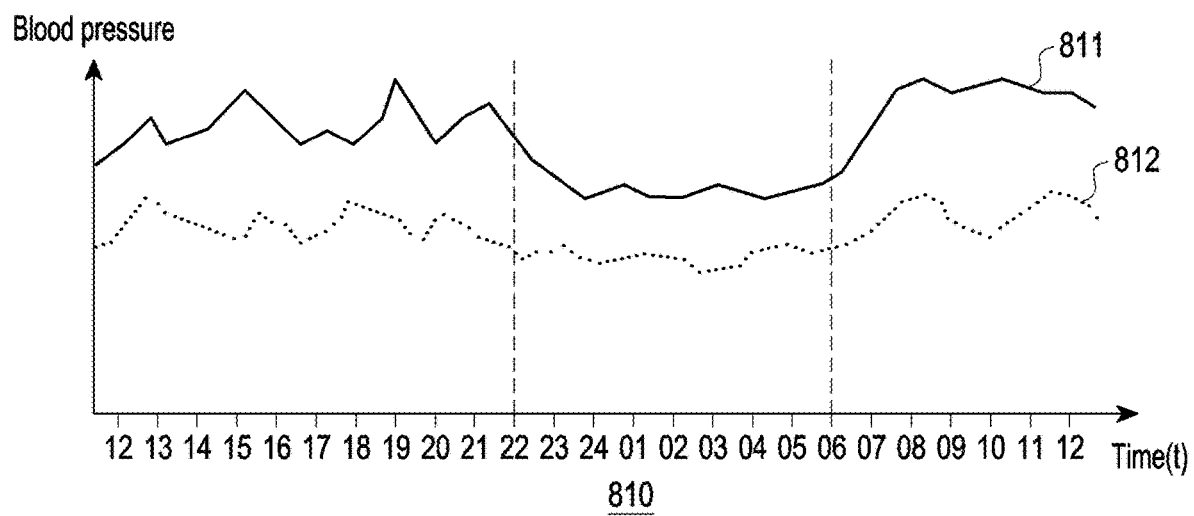
FIG. 8 includes graphs illustrating a change in blood pressure when apnea occurs in a sleep state, according to various embodiments.
Figure 8:
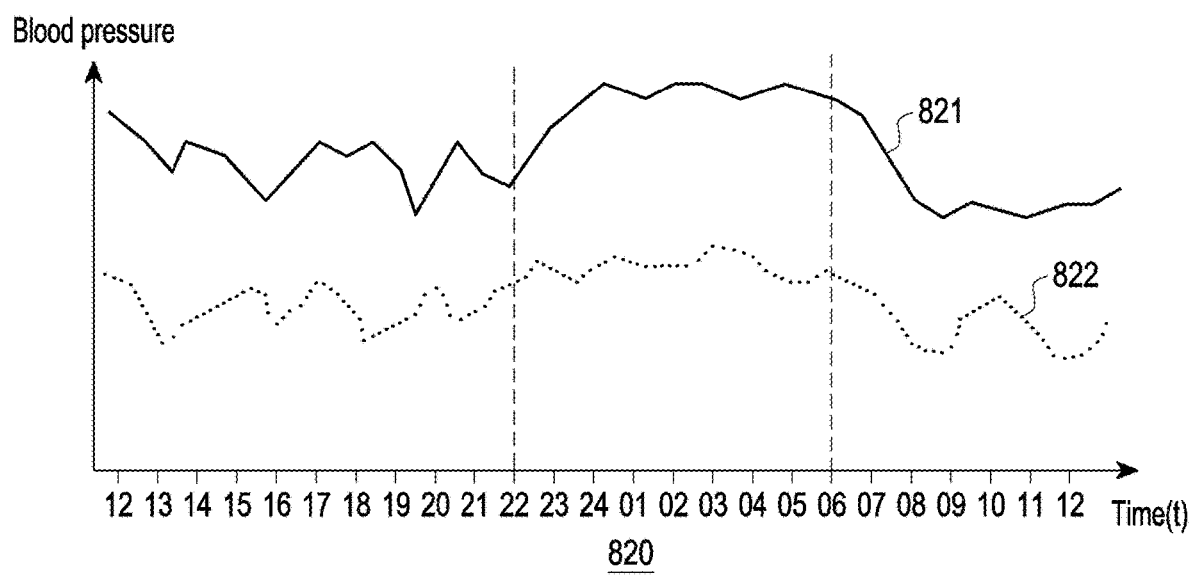

FIG. 8 includes graphs 800 illustrating a change in blood pressure when apnea occurs in a sleep state, according to various embodiments.

Referring to FIG. 8, in an embodiment, reference numeral 810 denotes the change in blood pressure over time for a user who did not have sleep apnea, and reference numeral 820 denotes the change in blood pressure over time for a user who has sleep apnea.

In an embodiment, as denoted by reference numeral 810, the systolic blood pressure (e.g., highest pressure) 811 and diastolic blood pressure (e.g., lowest pressure) 812 of the heart of the user without sleep apnea (or sleep apnea symptoms)) may be obtained (e.g., measured) as low in the sleep state (e.g., a state for a time period from when the time t is 22 o'clock to when the time t is 06 o'clock) as compared with the non-sleep state (e.g., states for a time period from when the time t is 12 o'clock to when the time t is 22 o'clock and a time period from when the time t is 06 o'clock to when the time t is 12 o'clock) (e.g., each stable state during non-sleep).

In an embodiment, as denoted by reference numeral 820, the systolic blood pressure (e.g., highest pressure) 821 and diastolic blood pressure (e.g., lowest pressure) 822 of the heart of the user with sleep apnea may be obtained (e.g., measured) as equal or high in the sleep state (e.g., a state for a time period from when the time t is 22 o'clock to when the time t is 06 o'clock) as compared with the non-sleep state (e.g., states for a time period from when the time t is 12 o'clock to when the time t is 22 o'clock and a time period from when the time t is 06 o'clock to when the time t is 12 o'clock) (e.g., each stable state during non-sleep).

In an embodiment, as described with reference to FIG. 8, the blood pressure obtained in the sleep state of the user with sleep apnea may be equal to or larger than the blood pressure obtained in the non-sleep state (or the blood pressure obtained in the case where apnea does not occur during sleep).

In an embodiment, unlike in FIG. 8, the blood pressure in the sleep state of the user without sleep apnea may be less than the blood pressure in the non-sleep state by about 15% or more whereas the blood pressure of the user with sleep apnea may be smaller than the blood pressure in the non-sleep state within a range of about 5% to about 15% of the blood pressure in the non-sleep state.

In an embodiment, the processor 350 may reduce the power consumption in the electronic device 101 by obtaining the blood pressure through the sensor 330 during a designated time and detecting sleep apnea based on the blood pressure obtained during the designated time if the first value indicated by the first biometric information is reduced so that the difference between the first value and the second value becomes a designated value or more.

Referring back to FIG. 4, in operation 409, in an embodiment, the processor 350 may provide information related to the user's apnea based on the obtained second biometric information and the second biometric information obtained in the designated state.

In an embodiment, the processor 350 may provide information related to the user's apnea based on the obtained second biometric information and the second biometric information obtained in the designated state after the user's sleep state ends. For example, the processor 350 may obtain, through the first sensor 331 (e.g., an acceleration sensor), information about the movement of the electronic device 101 (e.g., the magnitude of the movement of the electronic device 101 or a change in the movement of the electronic device 101). The processor 350 may detect the termination of the user's sleep state (e.g., the user wakes up from sleep) based on the information about the movement of the electronic device 101. When the termination of the user's sleep state is detected, the processor 350 may provide information related to the user's apnea based on the obtained second biometric information and the second biometric information obtained in the designated state.

In an embodiment, the processor 350 may compare the second biometric information (e.g., at least one of the oxygen saturation or the blood pressure obtained in operation 407), which is obtained (has been obtained) in operation 407, with the second biometric information obtained in the stable state during non-sleep, as the designated state.

In an embodiment, the processor 350 may detect, through the first sensor 331, that the user is in the stable state during non-sleep. When it is detected that the user is in the stable state during non-sleep, the processor 350 may obtain the second biometric information (e.g., at least one of the oxygen saturation or the blood pressure) through the second sensor 333 (e.g., a PPG sensor) during the designated time (or while in the non-sleep state and stable state).

In an embodiment, the processor 350 may obtain the second biometric information through the second sensor 333 whenever it is detected that the user is in the non-sleep state and the stable state.

In an embodiment, if a plurality of second biometric information is obtained over a plurality of times in the stable state during non-sleep, the processor 350 may determine the value of the second biometric information (hereinafter, referred to as a 'second value of second biometric information') obtained through operation 407, based on the plurality of second biometric information.

In an embodiment, if the plurality of second biometric information is obtained over a plurality of times in the stable state during non-sleep, the processor 350 may determine that the smallest (or lowest) value of the values indicated by each of the plurality of second biometric information is the second value of the second biometric information.

In an embodiment, if a plurality of second biometric information is obtained over a plurality of times in the stable state during non-sleep, the processor 350 may determine that the largest (or highest) value among the values indicated by each of the plurality of second biometric information is the second value of the second biometric information.

In an embodiment, if a plurality of second biometric information is obtained over a plurality of times in the stable state during non-sleep, the processor 350 may determine that the average of the values indicated by each of the plurality of second biometric information is the second value of the second biometric information.

In an embodiment, the processor 350 may obtain a plurality of second biometric information over a plurality of times in the stable state during non-sleep, daily (e.g., on a daily cycle) during a designated period (e.g., about one week). The processor 350 may determine (e.g., calculate) the average of the plurality of first biometric information over a plurality of times in the stable state during non-sleep, daily, during the designated period (e.g., the average of the values indicated by the plurality of second biometric information obtained in each stable state during non-sleep during each day in the designated period). The processor 350 may determine the lowest value among the average values of the plurality of second biometric information about each of the days included in the designated period as the second value of the second biometric information.

In an embodiment, the processor 350 may store the second value of the second biometric information determined based on the second biometric information obtained in the stable state during non-sleep, as the designated state, in the memory 340 or may transmit the second value through the communication module 310 to another electronic device (e.g., the electronic device 102, the electronic device 104, or the server 108).

In an embodiment, the processor 350 may update the second value of the second biometric information as the second biometric information is obtained in the stable state during non-sleep.

In an embodiment, the processor 350 may detect the occurrence of sleep apnea (or a high chance of an occurrence of sleep apnea) by comparing the first value of the second biometric information and the second value of the second biometric information.

In an embodiment, if the oxygen saturation value (e.g., the numerical value of the oxygen saturation) obtained through operation 407 is smaller (or lower) than the oxygen saturation value obtained in the stable state during non-sleep by a designated value (e.g., about 15%) or more, the processor 350 may determine that sleep apnea has occurred.

In an embodiment, if the oxygen saturation value obtained through operation 407 is reduced to be smaller than the oxygen saturation value obtained in the stable state during non-sleep by a designated value (e.g., about 15%) or more, the processor 350 may determine that sleep apnea has occurred.

In an embodiment, if such a pattern is detected in which the oxygen saturation value obtained through operation 407 is reduced to be smaller than the oxygen saturation value obtained in the stable state during non-sleep by a designated value (e.g., about 15%) or more and is then increased, the processor 350 may determine that sleep apnea has occurred.

In an embodiment, if the blood pressure value (e.g., the numerical value of the blood pressure) obtained through operation 407 is equal to (or maintained) or larger than the blood pressure value obtained in the stable state during non-sleep, the processor 350 may determine that sleep apnea has occurred. However, without being limited thereto, according to an embodiment, even when the blood pressure value (e.g., the numerical value of the blood pressure) obtained through operation 407 is smaller than the blood pressure value obtained in the stable state during non-sleep by a designated value or less (e.g., not more than the blood pressure value corresponding to about 10% of the blood pressure obtained in the stable state during non-sleep), the processor 350 may determine that sleep apnea has occurred. In an embodiment, the blood pressure in the sleep state of the user without sleep apnea may be less than the blood pressure in the non-sleep state by about 15% or more whereas the blood pressure of the user with sleep apnea may be smaller than the blood pressure in the non-sleep state within a range of about 5% to about 15% of the blood pressure in the non-sleep state.

In an embodiment, when the occurrence of sleep apnea is detected, the processor 350 may provide information related to the user's sleep apnea.

A method for providing information related to the user's sleep apnea when the occurrence of sleep apnea is detected is described in greater detail below with reference to FIGS. 9 and 10.

Figure 9:
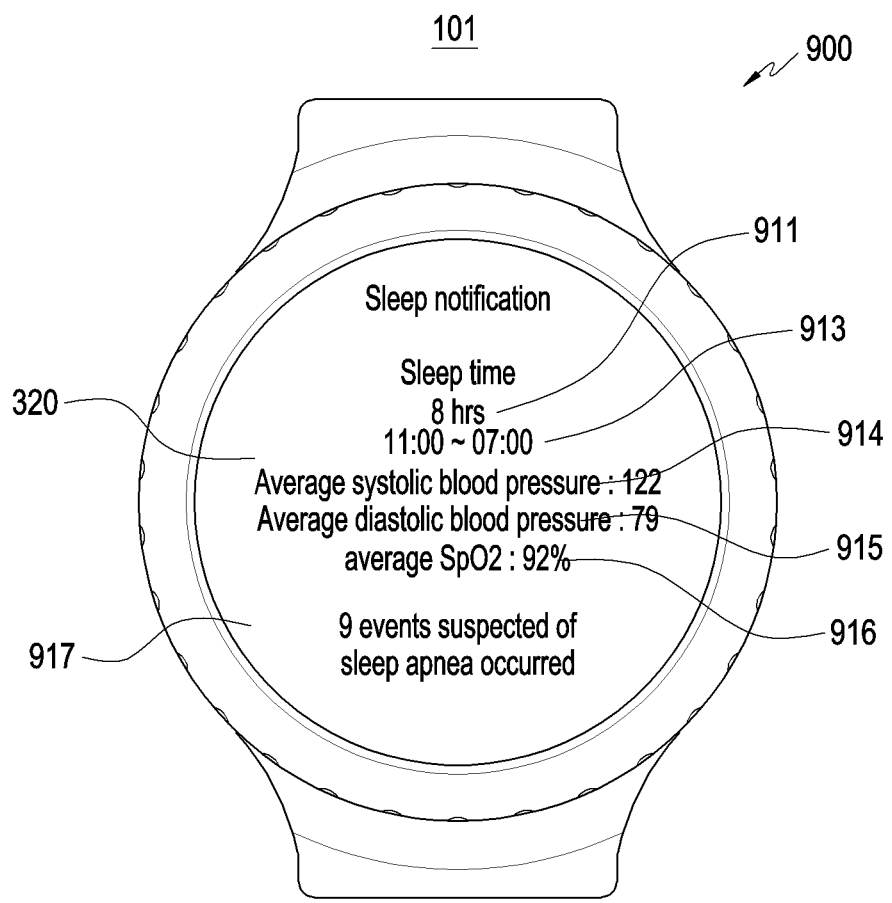
FIG. 9 is an diagram illustrating an example method for providing information related to sleep apnea in an electronic device, according to various embodiments.

FIG. 9 is a diagram 900 illustrating an example method for providing information related to sleep apnea in an electronic device 101, according to various embodiments.

Figure 10:
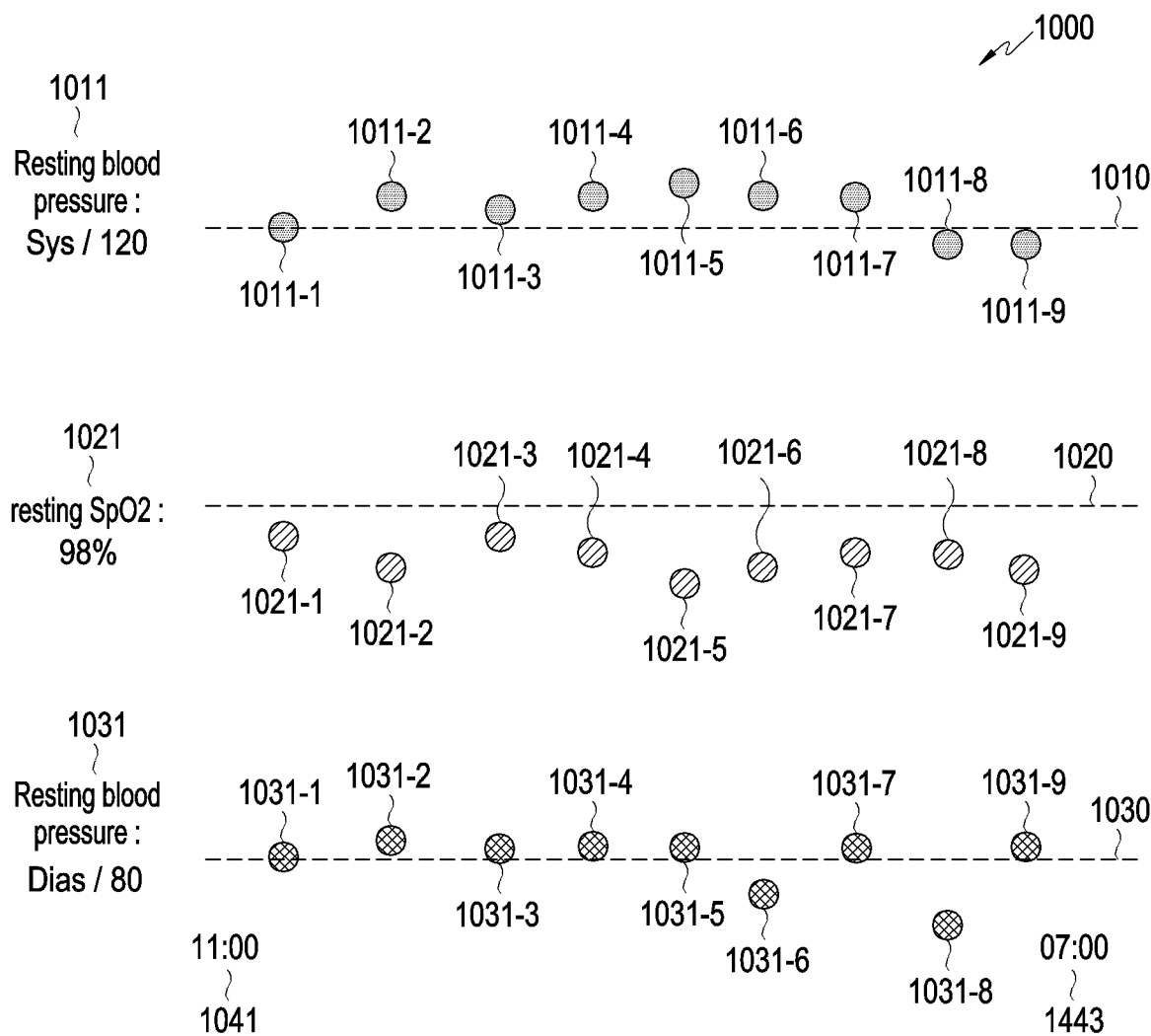
FIG. 10 is a diagram illustrating an example method for providing information related to sleep apnea in an external electronic device, according to various embodiments.

FIG. 10 is a diagram 1000 illustrating an example method for providing information related to sleep apnea in an external electronic device, according to various embodiments.

Referring to FIGS. 9 and 10, in an embodiment, the processor 350 may display information related to the user's sleep apnea through the display 320 as illustrated in FIG. 9. For example, the processor 350 may display, through the display 320, information 911 and 913 about the time when the user is in the sleep state, the average systolic blood pressure 914 of the heart, the average diastolic blood pressure 915 of the heart, the average 916 of the obtained oxygen saturation values, and information 917 indicating the number of times in which sleep apnea has been detected and the detection of sleep apnea (e.g., information indicating that the user is highly likely to be in obstructive sleep apnea). However, information displayed through the electronic device 101 is not limited to the examples of FIG. 9.

In an embodiment, the processor 350 may transmit information about the obtained second biometric information and sleep apnea-related information through the communication module 310 to an external electronic device (e.g., a smartphone interworking with the electronic device 101) (e.g., the electronic device 102 or the electronic device 104).

In an embodiment, as illustrated in FIG. 10, the external electronic device may display the information about the second biometric information and sleep apnea-related information received from the electronic device 101. For example, the external electronic device may display sleep start time information 1041, sleep end time information 1443, information 1011 indicating the numerical value of the systolic blood pressure obtained in the stable state, objects 1011-1 to 1011-9 indicating the numerical values of the systolic blood pressure when apnea is detected during sleep together with an object 1010 indicating the numerical value of the systolic blood pressure obtained in the stable state, information 1021 indicating the numerical value of the oxygen saturation obtained in the steady state, objects 1021-1 to 1021-9 indicating the numerical values of the oxygen saturation when apnea is detected during sleep together with an object 1020 indicating the numerical value of the oxygen saturation obtained in the stable state, information 1031 indicating the numerical value of the diastolic blood pressure obtained in the stable state, and objects 1031-1 to 1031-9 indicating the numerical values of the diastolic blood pressure when apnea is detected during sleep together with an object 1030 indicating the numerical value of the diastolic blood pressure obtained in the stable state. However, information displayed through the other electronic device is not limited to the examples of FIG. 10.

Although not described through FIGS. 4 to 10, in an embodiment, the electronic device 101 (or an external electronic device communicatively connected with the electronic device 101) may transmit the information, obtained while performing the operations for detecting sleep apnea, to a server (e.g., the server 108).

In an embodiment, the electronic device 101 may provide information related to sleep apnea through an external electronic device operatively connected with the electronic device 101. For example, the electronic device 101 may provide information related to sleep apnea through an external electronic device connected through short-range communication (e.g., Wi-Fi or Bluetooth) in an Internet of things (IoT) environment. The electronic device 101 may provide information related to sleep apnea through an external electronic device connected with the same account through a server.

Figure 11:
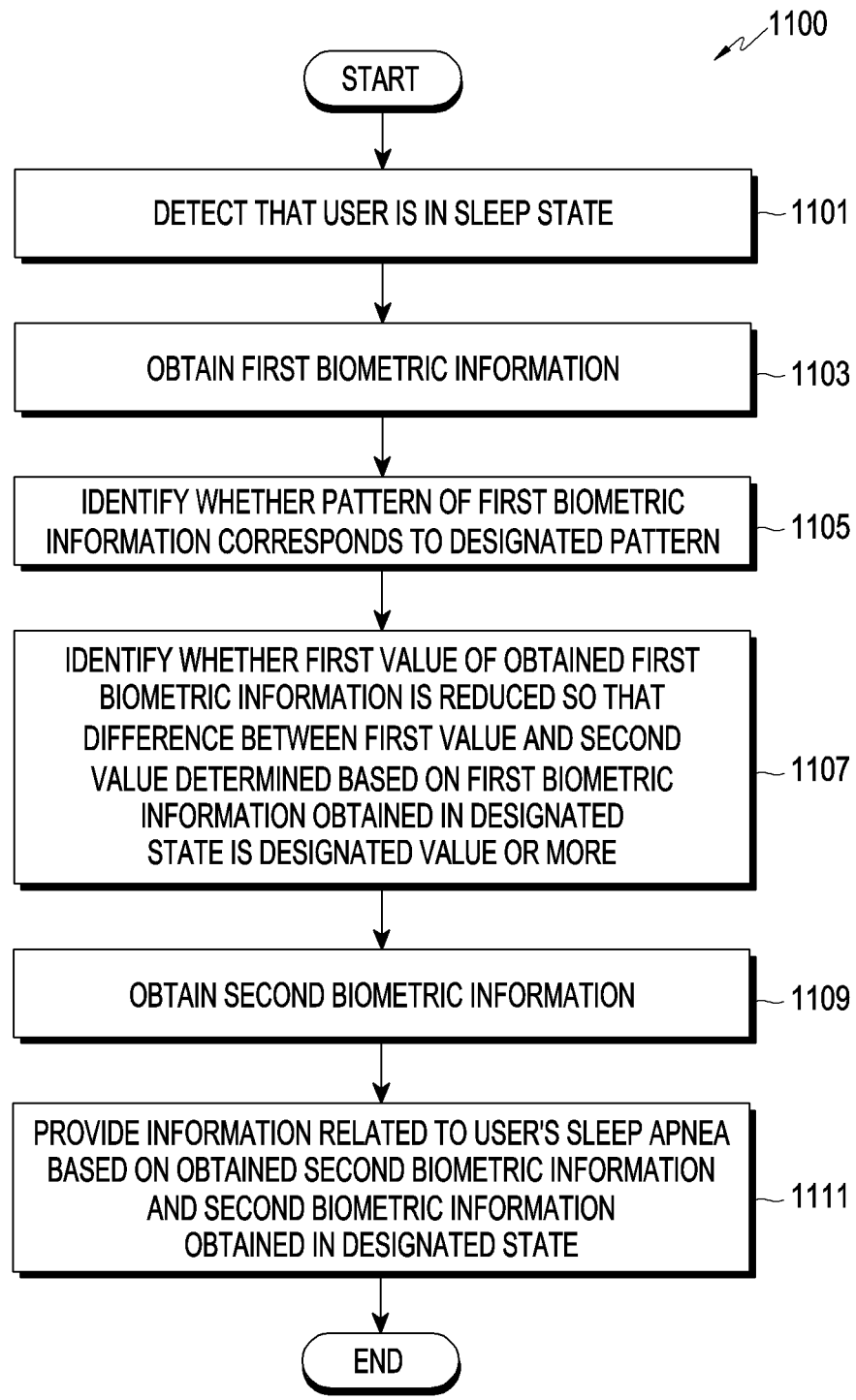
FIG. 11 is a flowchart illustrating an example method for detecting sleep apnea, according to various embodiments.

FIG. 11 is a flowchart 1100 illustrating an example method for detecting sleep apnea, according to various embodiments.

Referring to FIG. 11, in operation 1101, in an embodiment, the processor 350 may detect, through the sensor 330, that the user of the electronic device 101 is in a sleep state.

In operation 1103, in an embodiment, if it is detected that the user is in the sleep state, the processor 350 may obtain the user's first biometric information through the sensor 330. The examples of operations 1101 and 1103 of FIG. 11 are at least partially the same or similar to the examples of operations 401 and 403 of FIG. 4, no detailed description thereof is presented below.

In operation 1105, in an embodiment, the processor 350 may identify whether a pattern (e.g., a change in the first biometric information being obtained) indicated by the first biometric information (e.g., the first biometric information obtained by performing operation 1103) corresponds to a designated pattern.

In an embodiment, the designated pattern may be a pattern in which the user's pulse obtained during sleep becomes bradycardia and then changes to tachycardia. In an embodiment, the designated pattern may be a pattern in which the obtained pulse rate is reduced to be not more than a designated value as compared with the pulse rate obtained in a designated state (e.g., the designated state described through operation 405 of FIG. 4) and is then increased to be not less than the minimum pulse rate (e.g., about 90 beats) of tachycardia.

In an embodiment, the processor 350 may identify whether the pattern of the first biometric information corresponding to the designated pattern is detected a designated number of times or more during a designated time. For example, the processor 350 may identify whether the pattern of the first biometric information corresponding to the designated pattern is detected five times or more for about one hour after the sleep state starts. In an embodiment, if the user with sleep apnea (e.g., obstructive sleep apnea) has seven hours of sleep time, apnea which lasts about 10 seconds or more may occur 30 times or more (e.g., apnea which lasts about 10 seconds or more for one hour occurs five times or more).

In operation 1105, if the processor 350 identifies that the pattern indicated by the first biometric information corresponds to the designated pattern (e.g., if the pattern of the first biometric information corresponding to the designated pattern is detected a designated number of times or more during a designated time), the processor 350 may identify whether the first value indicated by the obtained first biometric information is reduced so that the difference between the first value and the second value determined based on the first biometric information obtained in the designated state becomes a designated value or more, in operation 1107.

Since the examples of operation 1107 are at least partially the same or similar to the examples of operation 405 of FIG. 4, a detailed description thereof may not be repeated here. In operation 1109, according to an embodiment, if the first value indicated by the first biometric information is reduced so that the difference between the first value and the second value becomes a designated value or more, the processor 350 may obtain second biometric information through the sensor 330.

In operation 1111, in an embodiment, the processor 350 may provide information related to the user's apnea based on the obtained second biometric information and the second biometric information obtained in the designated state.

Since the examples of operations 1109 and 1111 are at least partially the same or similar to the examples of operations 407 and 409 of FIG. 4, a detailed description thereof may not be repeated here.

Figure 12:
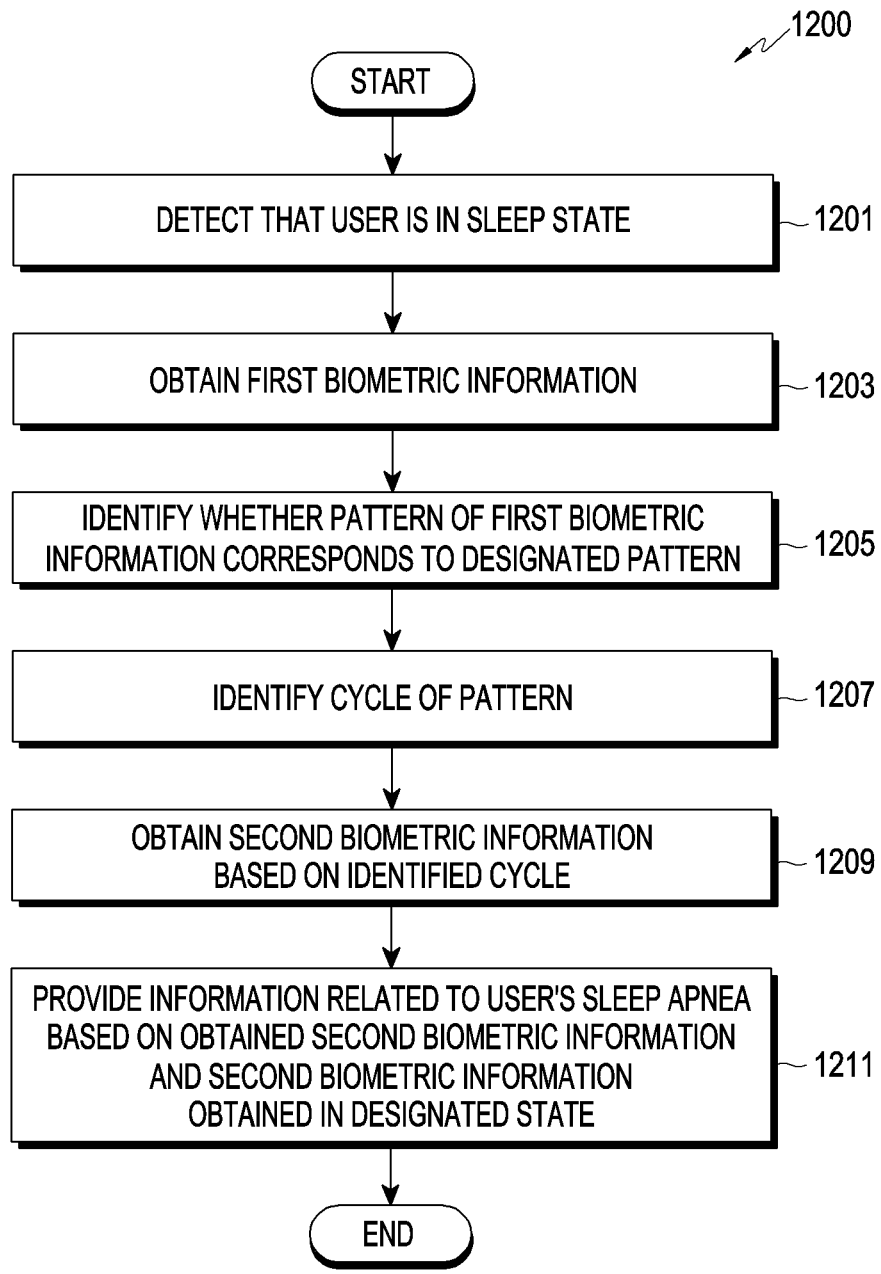
FIG. 12 is a flowchart illustrating an example method for detecting sleep apnea, according to various embodiments.

FIG. 12 is a flowchart 1200 illustrating an example method for detecting sleep apnea, according to various embodiments.

Referring to FIG. 12, in operation 1201, in an embodiment, the processor 350 may detect, through the sensor 330, that the user of the electronic device 101 is in a sleep state.

In operation 1203, in an embodiment, if it is detected that the user is in the sleep state, the processor 350 may obtain the user's first biometric information through the sensor 330.

Since the examples of operations 1201 and 1203 of FIG. 12 are at least partially the same or similar to the examples of operations 1101 and 1103 of FIG. 11, a detailed description thereof may not be repeated here.

In operation 1205, in an embodiment, the processor 350 may identify whether a pattern (e.g., a change in the first biometric information being obtained) indicated by the first biometric information (e.g., the first biometric information obtained by performing operation 1203) corresponds to a designated pattern.

Since the examples of operation 1205 are at least partially the same or similar to the examples of operation 1105 of FIG. 11, a detailed description thereof may not be repeated here. In operation 1205, if the processor 350 identifies that the pattern indicated by the first biometric information corresponds to the designated pattern (e.g., if the pattern of the first biometric information corresponding to the designated pattern is detected a designated number of times or more during a designated time), the processor 350 may identify the cycle of the pattern indicated by the first biometric information in operation 1207, according to an embodiment. For example, the processor 350 may identify the cycle, in which the pattern of the first biometric information occurs, if the pattern of the first biometric information corresponding to the designated pattern is detected the designated number of times during the designated time.

In an embodiment, the pattern of the first biometric information corresponding to the designated pattern, occurring to the user with sleep apnea, may occur periodically (e.g., at regular time intervals). According to an embodiment, it is possible to predict the times when the pattern of the first biometric information corresponding to the designated pattern is to occur after the current time, based on the cycle in which the pattern of the first biometric information corresponding to the designated pattern occurs and the time when the pattern of the first biometric information corresponding to the designated pattern occurred before the current time. In operation 1209, according to an embodiment, the processor 350 may obtain the second biometric information through the sensor 330 (e.g., the second sensor 333) based on the cycle of the pattern of the first biometric information corresponding to the designated pattern. For example, the processor 350 may obtain the second biometric information at each cycle of the pattern of the first biometric information corresponding to the designated pattern from the time when the pattern of the first biometric information corresponding to the designated pattern occurred before the current time.

In operation 1211, in an embodiment, the processor 350 may provide information related to the user's apnea based on the obtained second biometric information and the second biometric information obtained in the designated state.

Since the examples of operation 1211 are at least partially the same or similar to the examples of operation 1111 of FIG. 11, a detailed description thereof may not be repeated here.

According to various example embodiments of the disclosure, a method for detecting sleep apnea by an electronic device may comprise: detecting that a user of the electronic device is in a sleep state, based on detecting that the user is in the sleep state, obtaining first biometric information, identifying whether a first value indicated by the obtained first biometric information is decreased so that a difference between the first value and a second value determined based on first biometric information obtained in a designated state is a designated value or more, based on the first value being decreased so that the difference between the first value and the second value is the designated value or more, obtaining second biometric information, and providing information related to sleep apnea based on the obtained second biometric information and second biometric information obtained in the designated state.

According to various example embodiments, the first biometric information may include a pulse, and the second biometric information may include at least one of an oxygen saturation or a blood pressure.

According to various example embodiments, the method may further comprise determining the second value of the first biometric information based on the first biometric information obtained in a stable state during non-sleep as the designated state.

According to various example embodiments, determining the second value of the first biometric information may include obtaining a plurality of first biometric information over a plurality of times in the stable state during non-sleep, through the at least one sensor and determining a smallest value among a plurality of values indicated by each of the plurality of first biometric information, as a second value of the first biometric information.

According to various example embodiments, the method may further comprise obtaining a plurality of first biometric information while the user is in the sleep state as the designated state and determining an average of values, except for values not less than a designated first value and not more than a designated second value, among values indicated by the plurality of first biometric information, as a second value of the first biometric information.

According to various example embodiments, obtaining the second biometric information may include identifying a time when the first value is reduced so that the difference between the first value and the second value is the designated value or more and obtaining the second biometric information during a designated time from the time.

According to various example embodiments, providing the information related to sleep apnea may include identifying a third value indicated by the obtained second biometric information, identifying a fourth value of second biometric information determined based on the second biometric information obtained in the user's stable state during non-sleep as the designated state, and providing information related to the user's sleep apnea, based on the third value and the fourth value.

According to various example embodiments, identifying whether the first value is reduced so that the difference between the first value and the second value is the designated value or more may include identifying whether a pattern indicated by the first biometric information corresponds to a designated pattern, identifying whether the pattern corresponding to the designated pattern is detected a designated number of times during a designated time, and if the pattern corresponding to the designated pattern is detected the designated number of times during the designated time, identifying whether the first value is reduced so that the difference between the first value and the second value is the designated value or more.

According to various example embodiments, the method may further comprise identifying whether a pattern indicated by the first biometric information corresponds to a designated pattern, identifying a cycle of the pattern if the pattern corresponds to the designated pattern, and obtaining the second biometric information based on the cycle of the pattern. According to various example embodiments, obtaining the first biometric information may include controlling at least one sensor of the electronic device to operate at a first sampling frequency to obtain the first biometric information, and obtaining the second biometric information may include controlling the at least one sensor to operate at a second sampling frequency higher than the first sampling frequency to obtain the second biometric information. Further, the structure of the data used in embodiments of the disclosure may be recorded in a non-transitory computer-readable recording medium via various means. The computer-readable recording medium includes a storage medium, such as a magnetic storage medium (e.g., a ROM, a floppy disc, or a hard disc) or an optical reading medium (e.g., a CD-ROM or a DVD).

Example embodiments of the disclosure have been described above. The above-described embodiments are merely examples, and it will be appreciated by one of ordinary skill in the art various changes may be made thereto without departing from the scope of the present disclosure. Hence, the methods disclosed herein should be interpreted not as limiting but as illustrative. The scope of the present disclosure should be understood by the disclosure, including the following claims, and all technical spirits within equivalents thereof should be interpreted to belong to the scope of the present disclosure. It should also be understood that any of the embodiment(s) described herein may be used in conjunction with any other embodiment(s) described herein.

What is claimed is:

1. An electronic device, comprising:
    at least one sensor;
    at least one processor; and
    memory storing instructions that, when executed by the at least one processor, cause the electronic device to:
        detect, through the at least one sensor, that a user of the electronic device is in a sleep state,
        based on detecting that the user is in the sleep state, obtain first biometric information through the at least one sensor, the first biometric information including a pulse,
        identify whether a first value indicated by the obtained first biometric information is decreased so that a difference between the first value and a second value determined based on first biometric information obtained in a designated state is greater than or equal to a designated value, the designated state including a stable state during non-sleep, the first value and the second value being pulse rates,
        based on identifying that first value is decreased so that the difference between the first value and the second value is greater than or equal to the designated value, obtain second biometric information through the at least one sensor, the second biometric information including at least one of an oxygen saturation or a blood pressure, and
        provide information related to sleep apnea based on the obtained second biometric information and second biometric information obtained in the designated state.

2. The electronic device of claim 1, wherein the instructions, when executed by the at least one processor, cause the electronic device to:
    obtain a plurality of first biometric information over a plurality of times in the stable state during the non-sleep, through the at least one sensor, and
    determine a smallest value among a plurality of values indicated by each of the plurality of first biometric information, as the second value of the first biometric information.

3. The electronic device of claim 1, wherein the instructions, when executed by the at least one processor, cause the electronic device to:
    obtain a plurality of first biometric information, through the at least one sensor, while in the sleep state as the designated state, and
    determine an average of values, except for values not less than a designated first value and not more than a designated second value, among values indicated by the plurality of first biometric information, as the second value of the first biometric information.

4. The electronic device of claim 1, wherein the instructions, when executed by the at least one processor, cause the electronic device to:
    identify a time at which the first value is reduced so that the difference between the first value and the second value is the designated value or more, and
    obtain the second biometric information, through the at least one sensor, during a designated time from the time.

5. The electronic device of claim 1, wherein the instructions, when executed by the at least one processor, cause the electronic device to:
    identify a third value indicated by the obtained second biometric information,
    identify a fourth value of the second biometric information determined based on the second biometric information obtained in the stable state during the non-sleep as the designated state, and
    provide the information related to sleep apnea, based on the third value and the fourth value.

6. The electronic device of claim 1, wherein the instructions, when executed by the at least one processor, cause the electronic device to:
    identify whether a pattern indicated by the first biometric information corresponds to a designated pattern,
    identify whether the pattern corresponding to the designated pattern is detected a designated number of times during a designated time, and
    based on identifying that the pattern corresponding to the designated pattern is detected the designated number of times during the designated time, identify whether the first value is reduced so that the difference between the first value and the second value is greater than or equal to the designated value.

7. The electronic device of claim 1, wherein the instructions, when executed by the at least one processor, further cause the electronic device to:
    identify whether a pattern indicated by the first biometric information corresponds to a designated pattern,
    identify a cycle of the pattern based on identifying that the pattern corresponds to the designated pattern, and
    obtain the second biometric information, through the at least one sensor, based on the cycle of the pattern.

8. The electronic device of claim 1, wherein the instructions, when executed by the at least one processor, cause the electronic device to:
    control the at least one sensor to operate at a first sampling frequency to obtain the first biometric information, and
    control the at least one sensor to operate at a second sampling frequency higher than the first sampling frequency to obtain the second biometric information.

9. A method for detecting sleep apnea by an electronic device, the method comprising:
  detecting that a user of the electronic device is in a sleep state through at least one sensor of the electronic device;
  based on detecting that the user is in the sleep state, obtaining first biometric information through the at least one sensor, the first biometric information including a pulse;
  identifying whether a first value indicated by the obtained first biometric information is decreased so that a difference between the first value and a second value determined based on first biometric information obtained in a designated state is greater than or equal to a designated value, the designated state including a stable state during non-sleep, the first value and the second value being pulse rates;
  based on identifying that the first value is decreased so that the difference between the first value and the second value is greater than or equal to the designated value, obtaining second biometric information, the second biometric information including at least one of an oxygen saturation or a blood pressure; and
  providing information related to sleep apnea based on the obtained second biometric information and second biometric information obtained in the designated state.

10. The method of claim 9, wherein determining the second value of the first biometric information comprising:
  obtaining a plurality of first biometric information over a plurality of times in the stable state during the non-sleep, through at least one sensor; and
  determining a smallest value among a plurality of values indicated by each of the plurality of first biometric information, as the second value of the first biometric information.

11. The method of claim 9, further comprising:
  obtaining a plurality of first biometric information in the sleep state as the designated state; and
  determining an average of values, except for values not less than a designated first value and not more than a designated second value, among values indicated by the plurality of first biometric information, as the second value of the first biometric information.

12. The method of claim 9, wherein obtaining the second biometric information comprises:
  identifying a time at which the first value is reduced so that the difference between the first value and the second value is the designated value or more; and
  obtaining the second biometric information during a designated time from the time.

13. The method of claim 9, wherein providing the information related to the sleep apnea comprises:
  identifying a third value indicated by the obtained second biometric information;
  identifying a fourth value of the second biometric information determined based on the second biometric information obtained in the stable state during the non-sleep as the designated state; and
  providing the information related to sleep apnea, based on the third value and the fourth value.

14. The method of claim 9, wherein identifying whether the first value is reduced so that the difference between the first value and the second value is the designated value or more comprises:
  identifying whether a pattern indicated by the first biometric information corresponds to a designated pattern;
  identifying whether the pattern corresponding to the designated pattern is detected a designated number of times during a designated time; and
  based on identifying that the pattern corresponding to the designated pattern is detected the designated number of times during the designated time, identifying whether the first value is reduced so that the difference between the first value and the second value is the designated value or more.

15. The method of claim 9, further comprising:
  identifying whether a pattern indicated by the first biometric information corresponds to a designated pattern;
  identifying a cycle of the pattern if the pattern corresponds to the designated pattern; and
  obtaining the second biometric information based on the cycle of the pattern.

16. The method of claim 9, wherein obtaining the first biometric information comprises controlling at least one sensor of the electronic device to operate at a first sampling frequency to obtain the first biometric information, and
  wherein obtaining the second biometric information comprises controlling the at least one sensor to operate at a second sampling frequency higher than the first sampling frequency to obtain the second biometric information.

* * * * *